(12) United States Patent
Liu

(10) Patent No.: US 11,806,145 B2
(45) Date of Patent: Nov. 7, 2023

(54) PHOTOGRAPHING PROCESSING METHOD BASED ON BRAIN WAVE DETECTION AND WEARABLE DEVICE

(71) Applicant: BOE TECHNOLOGY GROUP CO., LTD., Beijing (CN)

(72) Inventor: Kairan Liu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 548 days.

(21) Appl. No.: 16/311,159

(22) PCT Filed: Mar. 20, 2018

(86) PCT No.: PCT/CN2018/079676
§ 371 (c)(1),
(2) Date: Dec. 18, 2018

(87) PCT Pub. No.: WO2019/001030
PCT Pub. Date: Jan. 3, 2019

(65) Prior Publication Data
US 2020/0214612 A1    Jul. 9, 2020

(30) Foreign Application Priority Data
Jun. 29, 2017    (CN) .......................... 201710516847.9

(51) Int. Cl.
*A61B 5/16* (2006.01)
*G06F 3/01* (2006.01)

(52) U.S. Cl.
CPC .............. *A61B 5/165* (2013.01); *G06F 3/015* (2013.01)

(58) Field of Classification Search
None
See application file for complete search history.

(56) References Cited

U.S. PATENT DOCUMENTS

| 2003/0156304 A1* | 8/2003 | Fedorovskaya .... G06K 9/00315 358/527 |
| 2006/0217598 A1* | 9/2006 | Miyajima ............ A61B 5/6887 600/300 |
| 2010/0070987 A1 | 3/2010 | Amento et al. |

(Continued)

FOREIGN PATENT DOCUMENTS

| CN | 101437116 A | 5/2009 |
| CN | 103327270 A | 9/2013 |

(Continued)

OTHER PUBLICATIONS

Chinese Office Action dated Jan. 6, 2020, from application No. 201710516847.9.

(Continued)

*Primary Examiner* — Alex M Valvis
*Assistant Examiner* — Aurelie H Tu
(74) *Attorney, Agent, or Firm* — XSENSUS LLP

(57) ABSTRACT

The present disclosure discloses a photographing processing method based on brain wave detection and a wearable device. The method includes evaluating an emotional state of a user based on a detected brain wave signal of the user. The method includes obtaining an emotional tag that labels the emotional state and combining the emotional tag into a photo taken in the emotional state.

7 Claims, 19 Drawing Sheets

Evaluating an emotional state of a user based on a detected brain wave signal of the user — S101

Obtaining an emotional tag that labels the emotional state and combining the emotional tag into a photo taken in the emotional state — S102

(56) References Cited

U.S. PATENT DOCUMENTS

| | | | |
|---|---|---|---|
| 2013/0012790 A1* | 1/2013 | Horseman | A61B 5/14551 600/301 |
| 2014/0221866 A1* | 8/2014 | Quy | A61B 5/369 600/544 |
| 2014/0223462 A1* | 8/2014 | Aimone | G16H 40/67 725/10 |
| 2015/0178915 A1* | 6/2015 | Chatterjee | G06F 16/58 382/128 |
| 2015/0255045 A1* | 9/2015 | Li | G06T 13/80 345/629 |
| 2015/0305662 A1* | 10/2015 | Kilmer | A61B 5/0022 600/476 |
| 2015/0366497 A1* | 12/2015 | Cavuoto | G09B 19/00 434/236 |
| 2016/0027042 A1* | 1/2016 | Heeter | G06Q 30/0248 705/14.47 |
| 2016/0374605 A1* | 12/2016 | Pandian | G06K 9/3233 600/323 |
| 2017/0042439 A1* | 2/2017 | Yeow | A61B 5/165 |
| 2017/0330265 A1 | 11/2017 | Liao et al. | |
| 2019/0015033 A1* | 1/2019 | Sahin | G16H 20/70 |

FOREIGN PATENT DOCUMENTS

| | | |
|---|---|---|
| CN | 103654799 A | 3/2014 |
| CN | 103716542 A | 4/2014 |
| CN | 103888696 A | 6/2014 |
| CN | 104010132 A | 8/2014 |
| CN | 104166692 A | 11/2014 |
| CN | 104382593 A | 3/2015 |
| CN | 105830066 A | 8/2016 |
| CN | 106341608 A | 1/2017 |
| CN | 106527161 A | 3/2017 |
| CN | 107320114 A | 11/2017 |
| EP | 3 244 556 A1 | 11/2017 |
| WO | WO-2016/123777 A1 | 8/2016 |

OTHER PUBLICATIONS

Yuan, Haiyun, "Research on Emotion Classification Based on EEG Signals", Jan. 15, 2015, 43 pages.

Chinese Office Action dated Mar. 22, 2019, from application serial No. 201710516847.9.

International Search Report and Written Opinion dated May 30, 2018, from application serial No. PCT/CN2018/079676.

* cited by examiner

Metal electrodes of brain wave sensor, inserting into hair (like comb teeth) and contacting scalp when being wore

PHOTOGRAPHING PROCESSING METHOD BASED ON BRAIN WAVE DETECTION AND WEARABLE DEVICE

CROSS-REFERENCE TO RELATED APPLICATIONS

The present application is based upon International Application No. PCT/CN2018/079676, filed on Mar. 20, 2018, which claims priority to Chinese Patent Application No. 201710516847.9, entitled "PHOTOGRAPHING PROCESSING METHOD BASED ON BRAIN WAVE DETECTION, SYSTEM AND APPARATUS THEREOF" filed on Jun. 29, 2017, and the entire contents thereof are incorporated herein by reference.

TECHNICAL FIELD

The present disclosure relates to the field of information processing technology, and in particular, to a photographing processing method based on brain wave detection and a wearable device.

BACKGROUND

At present, photos have been widely used in daily production and life as they can fixate persons or objects. However, the photo usually only records two-dimensional image information of the person or object, and thus the information contained therein is limited. Obviously, the user requires the photo as a carrier recording life to carry more abundant information, therefore, it needs to enrich the information contained in the photo.

SUMMARY

According to arrangements in a first aspect of the present disclosure, there is provided a photographing processing method based on brain wave detection, including: evaluating an emotional state of a user based on a detected brain wave signal of the user. The method includes obtaining an emotional tag that labels the emotional state and combining the emotional tag into a photo taken in the emotional state.

In the photographing processing method based on brain wave detection according to an arrangement of the present disclosure, the emotional tag is combined into the photo taken in the emotional state in an invisible pattern form. The user is prompted to enter a viewing password responsive to the invisible pattern being triggered by the user to send a viewing request; and an input viewing password is verified according to a pre-stored password of a verification, and the invisible pattern is converted into a visible emotional tag responsive to determining the verification is passed.

According to arrangements in a second aspect of the present disclosure, there is provided a photographing processing method based on brain wave detection, including: evaluating an emotional state of a user based on a detected brain wave signal of the user. The method includes comparing the emotional state with a preset tension state threshold, responsive to determining that the emotional state is evaluated as being tense The method includes photographing a surrounding situation of the user, responsive to obtaining that the emotional state is greater than or equal to the tension state threshold by the comparing. The method includes adding GPS information to photographing information to be sent to a preset terminal or server for seeking help.

In the photographing processing method based on brain wave detection according to an arrangement of the present disclosure, an emotional state of a user is evaluated based on a detected brain wave signal of the user. The emotional state is compared with a preset tension state threshold, responsive to the emotional state being evaluated as being tense. A surrounding situation of the user is shot, responsive to obtaining that the emotional state is greater than or equal to the tension state threshold by the comparing. GPS information is added to photographing information to be sent to a preset terminal or server for seeking help.

According to arrangements in a third aspect of the present disclosure, there is provided a photographing processing method based on brain wave detection. The method includes evaluating an emotional state of a user based on a detected brain wave signal of the user, responsive to detecting that the user is shopping. The method includes photographing label information of current clothing and corresponding location information, responsive to evaluating that the emotional state is the user being interested in the current clothing. The method includes obtaining information of e-commerce having clothing the same as or similar to the current clothing by sending a picture obtained by photographing the current clothing to an e-commerce platform. The method includes providing the user with shopping report for the user to make selection by obtaining the label information, the location information and the information of the e-commerce corresponding to a plurality of interesting clothing.

In the photographing processing method based on brain wave detection according to an arrangement of the present disclosure, an emotional state of a user is evaluated based on a detected brain wave signal of the user, responsive to detecting that the user is shopping. Label information of current clothing and corresponding location information is photographed, responsive to evaluating that the emotional state is that the user is interested in the current clothing. Information of e-commerce having clothing the same as or similar to the current clothing is obtained by sending a picture obtained by photographing the current clothing to an e-commerce platform. The user is provided with shopping report for the user to make selection by obtaining the label information, the location information and the information of the e-commerce corresponding to a plurality of interesting clothing.

According to embodiments in a fourth aspect of the present disclosure, there is provided a photographing processing method based on brain wave detection. The method includes evaluating an emotional state of a user based on a detected brain wave signal of the user. The method includes photographing a current picture responsive to evaluating that the emotional state of the user is that the user is interested in a picture on a current LED advertising board, and generating a photo with black and white stripes corresponding to the picture according to stroboscopic information sent by the LED advertising board, wherein the stroboscopic information identifies a purchase link. The method includes decoding the photo with black and white stripes to provide the user with the purchase link responsive to detecting that the user views the photo within a preset time. The method includes prompting the user to view or delete the photo at a preset time point, responsive detecting that the user does not view the photo within the preset time.

In the photographing processing method based on brain wave detection according to an arrangement of the present disclosure, an emotional state of a user is evaluated based on a detected brain wave signal of the user. A current picture is photographed responsive to evaluating that the emotional state of the user is that the user is interested in a picture on a current LED advertising board, and a photo with black and white stripes corresponding to the picture is generated according to stroboscopic information sent by the LED advertising board. The photo with black and white stripes is decoded to provide the user with the purchase link responsive to detecting that the user views the photo within a preset time; and the user is prompted to view or delete the photo at a preset time point, responsive to detecting that the user does not view the photo within the preset time.

According to arrangements in a fifth aspect of the present disclosure, there is provided a wearable device for photographing based on brain wave detection, including: a photographing module, a brain wave detecting module, a processor, and a memory. The memory is connected to the photographing module and the brain wave detecting module, and the processor, by reading an executable program code stored in the memory, executes a program corresponding to the executable program code for implementing the photographing processing method based on brain wave detection according to the arrangements in the first aspect of the present disclosure.

In the wearable device for photographing based on brain wave detection according to an arrangement of the present disclosure, the emotional tag is combined into the photo taken in the emotional state in an invisible pattern form. The user is prompted to enter a viewing password responsive to triggering the invisible pattern by the user to send a viewing request. An input viewing password is verified according to a pre-stored verification password, and the invisible pattern is converted into a visible emotional tag responsive to determining the verification is passed.

According to arrangements in a sixth aspect of the present disclosure, there is provided a wearable device for photographing based on brain wave detection. The wearable device includes a photographing module, a brain wave detecting module, a processor, and a memory. The memory is connected to the photographing module and the brain wave detecting module, and the processor, by reading an executable program code stored in the memory, executes a program corresponding to the executable program code for implementing the photographing processing method based on brain wave detection according to the arrangements in the second aspect of the present disclosure.

In the wearable device for photographing based on brain wave detection according to an arrangement of the present disclosure, an emotional state of a user is evaluated based on a detected brain wave signal of the user. The emotional state is compared with a preset tension state threshold, responsive to evaluating that the emotional state is tense. A surrounding situation of the user is shot, responsive to obtaining that the emotional state is greater than or equal to the tension state threshold by the comparing. GPS information is added to photographing information to be sent to a preset terminal or server for seeking help.

According to arrangements in a seventh aspect of the present disclosure, there is provided a wearable device for photographing based on brain wave detection. The wearable device includes a photographing module, a brain wave detecting module, a processor, and a memory. The memory is connected to the photographing module and the brain wave detecting module, and the processor, by reading an executable program code stored in the memory, executes a program corresponding to the executable program code for implementing the photographing processing method based on brain wave detection according to the arrangements in the third aspect of the present disclosure.

In the wearable device for photographing based on brain wave detection according to an arrangement of the present disclosure, an emotional state of a user is evaluated based on a detected brain wave signal of the user, responsive to detecting that the user is shopping. Label information of current clothing and corresponding location information is photographed, responsive to evaluating that the emotional state is that the user is interested in the current clothing. Information of e-commerce having clothing the same as or similar to the current clothing is obtained by sending a picture obtained by photographing the current clothing to an e-commerce platform. The user is provided with shopping report for the user to make selection by obtaining the label information, the location information and the information of the e-commerce corresponding to a plurality of interesting clothing.

According to arrangements in an eighth aspect of the present disclosure, there is provided a wearable device for photographing based on brain wave detection. The wearable device includes a photographing module, a brain wave detecting module, a processor, and a memory. The processor, by reading an executable program code stored in the memory, executes a program corresponding to the executable program code for implementing the photographing processing method based on brain wave detection according to the arrangements in the fourth aspect of the present disclosure.

In the wearable device for photographing based on brain wave detection according to an arrangement of the present disclosure, an emotional state of a user is evaluated based on a detected brain wave signal of the user. A current picture is photographed responsive to evaluating that the emotional state of the user is that the user is interested in a picture on a current LED advertising board, and a photo with black and white stripes corresponding to the picture is generated according to stroboscopic information sent by the LED advertising board. The photo with black and white stripes is decoded to provide the user with the purchase link responsive to detecting that the user views the photo within a preset time. The user is prompted to view or delete the photo at a preset time point, responsive to detecting that the user does not view the photo within the preset time.

According to arrangements in a ninth aspect of the present disclosure, there is provided a photographing system based on brain wave detection. The photographing system includes a terminal device having a photographing module and a wearable device for brain wave detecting. The wearable device for brain wave detecting is configured to detect a brain wave signal of a user, and the terminal device is configured to implement the photographing method based on brain wave detection according to the arrangements in the first aspect of the present disclosure.

In the photographing processing system based on brain wave detection according to an arrangement of the present disclosure, the emotional tag is combined into the photo taken in the emotional state in an invisible pattern form. The user is prompted to enter a viewing password responsive to triggering the invisible pattern by the user to send a viewing request. An input viewing password is verified according to a pre-stored password of a verification, and the invisible pattern is converted into a visible emotional tag responsive to determining that the verification is passed.

According to arrangements in a tenth aspect of the present disclosure, there is provided a photographing system based on brain wave detection. The photographing system includes a terminal device having a photographing module and a wearable device for brain wave detecting. The wearable device for brain wave detecting is configured to detect a brain wave signal of a user, and the terminal device is configured to implement the photographing method based on brain wave detection according to the arrangements in the second aspect of the present disclosure.

In the photographing processing system based on brain wave detection according to an arrangement of the present disclosure, an emotional state of a user is evaluated based on a detected brain wave signal of the user. The emotional state is compared with a preset tension state threshold, responsive to determining that the emotional state is evaluated as being tense. A surrounding situation of the user is shot, responsive to obtaining that the emotional state is greater than or equal to the tension state threshold by the comparing. GPS information is added to photographing information to be sent to a preset terminal or server for seeking help.

According to arrangements in a eleventh aspect of the present disclosure, there is provided a photographing system based on brain wave detection. The photographing system includes a terminal device having a photographing module and a wearable device for brain wave detecting. The wearable device for brain wave detecting is configured to detect a brain wave signal of a user, and the terminal device is configured to implement the photographing method based on brain wave detection according to the arrangements in the third aspect of the present disclosure.

In the photographing processing system based on brain wave detection according to an arrangement of the present disclosure, an emotional state of a user is evaluated based on a detected brain wave signal of the user, responsive to detecting that the user is shopping. Label information of current clothing and corresponding location information is photographed, responsive to evaluating that the emotional state is that the user is interested in the current clothing. Information of e-commerce having clothing the same as or similar to the current clothing is obtained by sending a picture obtained by photographing the current clothing to an e-commerce platform. The user is provided with shopping report for the user to make selection by obtaining the label information, the location information and the information of the e-commerce corresponding to a plurality of interesting clothing.

According to arrangements in a twelfth aspect of the present disclosure, there is provided a photographing system based on brain wave detection. The photographing system includes a terminal device having a photographing module and a wearable device for brain wave detecting. The wearable device for brain wave detecting is configured to detect a brain wave signal of a user, and the terminal device is configured to implement the photographing method based on brain wave detection according to the arrangements in the fourth aspect of the present disclosure.

In the photographing processing system based on brain wave detection according to an arrangement of the present disclosure, an emotional state of a user is evaluated based on a detected brain wave signal of the user. A current picture is photographed responsive to evaluating that the emotional state of the user is that the user is interested in a picture on a current LED advertising board, and a photo with black and white stripes corresponding to the picture is generated according to stroboscopic information sent by the LED advertising board. The photo with black and white stripes is decoded to provide the user with the purchase link responsive to detecting that the user views the photo within a preset time. The user is prompted to view or delete the photo at a preset time point, responsive to detecting that the user does not view the photo within the preset time.

The additional aspects and advantages of the present disclosure will be set forth in part in the description which follows, and in part will be apparent from the description which follows or will be understood through the practice of the present disclosure.

BRIEF DESCRIPTION OF THE DRAWINGS

The above and/or additional aspects and advantages of the present disclosure will become apparent and be readily understood from the following description of the arrangements with reference to the drawings, wherein.

DETAILED DESCRIPTION

Figure 1:
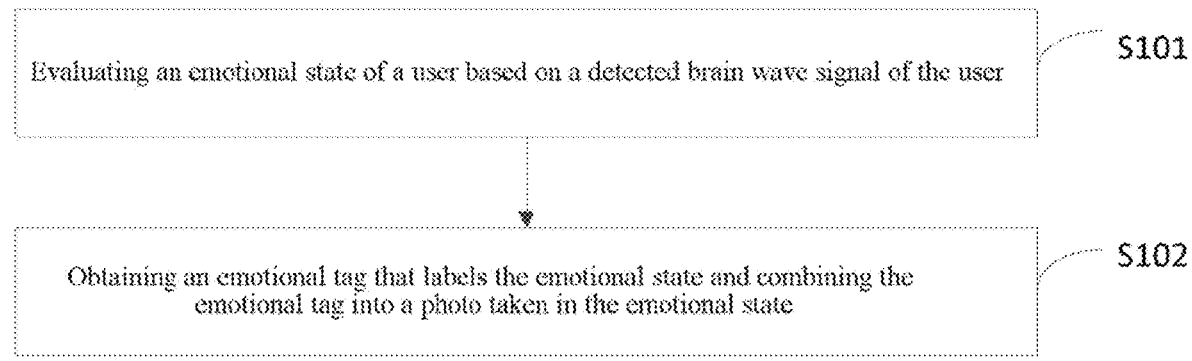
FIG. 1 is a flow chart of a photographing processing method based on brain wave detection according to a first arrangement of the present disclosure.

The arrangements of the present disclosure are described in detail below, and the examples of the arrangements are illustrated in the drawings, wherein the same or similar reference numerals are used to refer to the same or similar elements or elements having the same or similar functions throughout. The arrangements described below with reference to the accompanying drawings are illustrative, intended to explain the present disclosure, and are not to be construed as limiting of the present disclosure.

A photographing processing method and system based on brain wave detection and apparatus thereof according to an arrangement of the present disclosure will be described below with reference to the accompanying drawings.

It should be noted that in actual life, a user who takes a photo in a current state may have a special mood related to the current scene when taking a photo, and if the mood can be recorded in the photo taken in the current state, the information of the photo will be enriched, so that the user may avoid missing some wonderful moments in their lives and the like.

Thus, in the arrangement of the present disclosure, emotional information related to the mood in a photographing state is added to the photo to enrich the information carried in the photo.

Wherein it should be noted that the present disclosure describes an implementation process of adding related emotional information in a photo in combination with various application scenes. For convenience of description, the present disclosure is described based on the scenes.

It should be emphasized that the arrangements of the photographing processing method based on the brain wave detection in the various scenes described below with reference to the accompanying drawings may be separately implemented, or may be implemented in combination, for example, the photographing processing methods based on the brain wave detection in the first scene, the second scene, the third scene, and the fourth scene may be separately implemented, and the photographing processing methods based on the brain wave detection in the first and second scenes, or that in the first and third scenes, or that in the first, second and third scenes may be implemented in combination, which is not limited herein.

First Scene

In this scene, emotion of a user in a photographing state is combined into a photo in the form of a tag or the like.

FIG. 1 is a flow chart of a method of a photographing processing based on brain wave detection according to a first arrangement of the present disclosure, and as shown in FIG. 1, the method includes the following blocks.

In S101, an emotional state of a user is evaluated based on a detected brain wave signal of the user.

It can be understood that the brain waves are formed by a sum of postsynaptic potentials generated simultaneously by a large number of neurons when the brain is active. It records the change of the brain wave during brain activity, and is the overall response of the electrophysiological activity of the brain nerve cells on the surface of the scalp or the cerebral cortex. Therefore, in the arrangement of the present disclosure, the emotional state of the user is evaluated in combination with the brain wave that reflects the emotion of the user.

Specifically, since the brain waves are spontaneous rhythmic nerve electrical activities, they can be divided into frequency bands such as α wave, β wave, and γ wave according to changes in their frequencies. Therefore, according to different rhythm of nerve cell activity, the activity ranges of brain waves in different frequency bands are different. In the present arrangement, according to a large number of experiments, the correspondence between changes of brain waves in different frequency bands and user's emotions is obtained to evaluate the user's emotions according to the correspondence.

Specifically, in an arrangement of the present disclosure, variation diagrams of states of brain waves of different shapes and/or proportions of brain waves of different frequencies in a preset period may be obtained by analyzing the brain wave signal, and/or the emotional state of the user may be evaluated by calculating according to the variation diagrams of states of brain waves of different shapes and/or the proportions of brain waves of different frequencies in the preset period.

It should be noted that, in practical application, the detection of the user brain wave signal can be implemented in different manners according to different application scenes, which will be illustrated below by example.

As a possible implementation manner, the user's brain wave signal is detected by a plurality of brain wave sensing metal electrodes disposed at different positions on the inner wall of the headband.

Of course, in this example, in addition to the headband, the related brain wave detecting device may be disposed on any other device that can be worn on the head, such a hat, a helmet, a hair clip, etc., which is not limited herein.

In S102, an emotional tag that labels the emotional state is obtained and the emotional tag is combined into a photo taken in the emotional state.

Figure 2A:
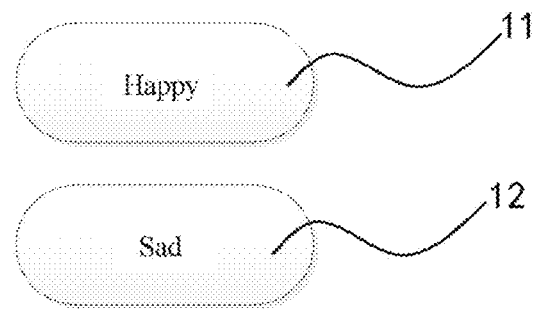
FIG. 2(a) is a schematic diagram of an emotional tag according to an arrangement of the present disclosure.
Figure 2B:
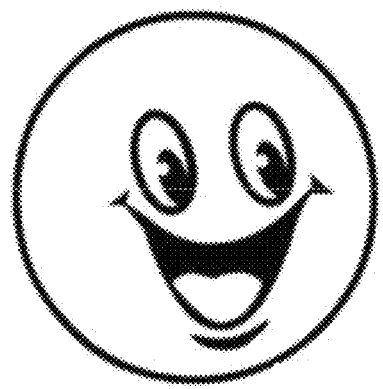
FIG. 2(b) is a schematic diagram of an emotional tag according to another arrangement of the present disclosure.
Figure 2C:
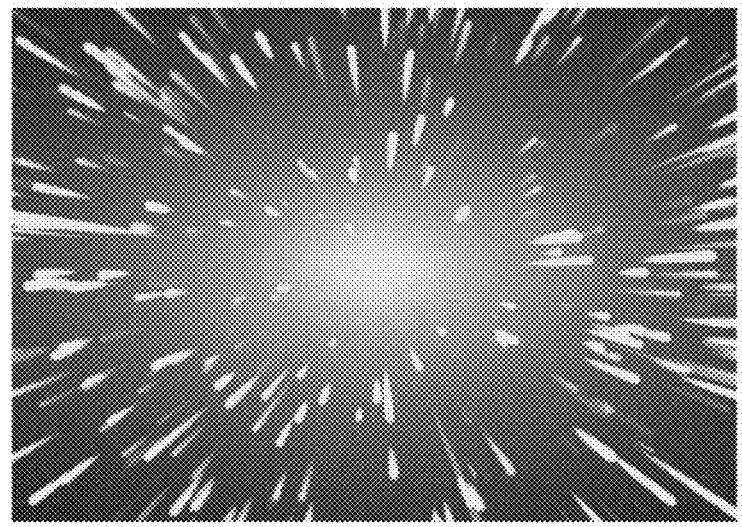
FIG. 2(c) is a schematic diagram of an emotional tag according to still another arrangement of the present disclosure.

The emotional tag may be a specific character tag, such as "happy" 11, "sad" 12, etc. shown in FIG. 2(a), or may be a specific facial expression pattern, such as facial expression patterns, etc., shown in FIG. 2(b), such as animation effects shown in FIG. 2(c).

Specifically, an emotional tag that labels the emotional state is obtained and the emotional tag is combined into a photo taken in the emotional state to record the emotion of the user in the current photographing state, so that the photo of the arrangement of the present disclosure can contain richer content compared to a normal photo.

In practical application, the emotional tag that labels the emotional state may be obtained in different ways according to specific application scenes, and the emotional tag may be combined into the photo taken in the emotional state, as illustrated below.

First Example

In this example, the emotional tag corresponding to the emotional state is pre-stored in an image library. Then, the emotional tag corresponding to the acquired emotional state is obtained by querying the pre-stored image library. Then, the emotional tag is added to a blank template preset in a camera. The emotional tag is adjusted to a suitable position for photographing after the camera performs image recognition on a main image.

Figure 3A:
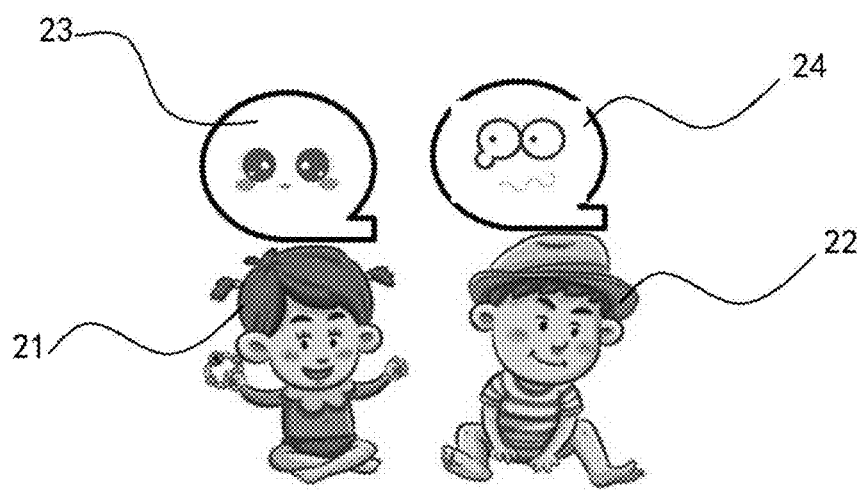
FIG. 3(a) is a schematic diagram showing a display position of an emotional tag according to an arrangement of the present disclosure.
Figure 3B:
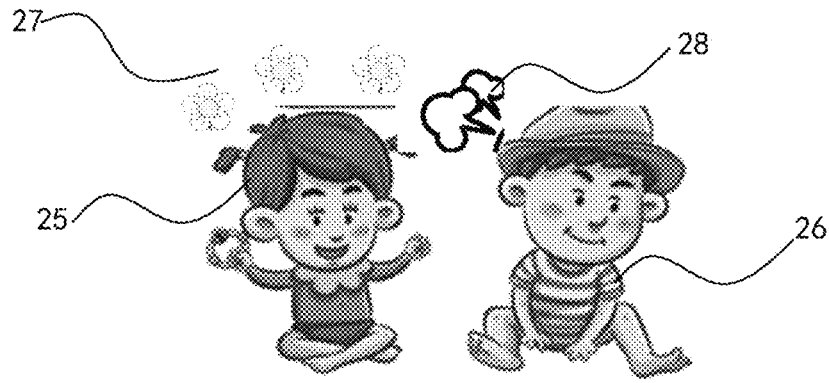
FIG. 3(b) is a schematic diagram showing a display position of an emotional tag according to another arrangement of the present disclosure.

Preferably, in this example, in order not to block the main body image, the position and size of the emotional tag can be adjusted in real time, that is, as shown in FIG. 3(a), an emotional tag in an animated form (which is shown with 23 and 24) may be displayed at the top of the main avatar (which is shown with 21 and 22). Of course, as shown in FIG. 3(b), in some application scenes, the emotional tag (which is shown with 27 and 28) can also be displayed on the original main image (which is shown with 25 and 26) in the form of an additional special effect.

For example, when the user sees wonderful scenery and then feels good, it shows by analyzing the brain waves that the user is in good mood at this moment. Then such signal is transmitted to a central processor, and thus an emotional tag related to the "pleasant" mood is obtained from the pre-stored image library. The location of the user in the photographing picture when taking a picture is confirmed by an image recognition technology. Then the emotional tag is displayed at a relevant position. Therefore, not only a normal person but also the emotional state of the user at this moment can be displayed when taking a picture by a camera.

Second Example

The emotional state is encoded and encoded code stream is transmitted to a driving circuit of a light emitting diode (LED) module, so that the driving circuit performs strobe according to the encoded code stream. For example, 0 in the code corresponds to that the driving circuit drives the LED module to be turned off, and 1 in the code corresponds to that the driving circuit drives the LED module to be turned on. A photo with black and white stripes is generated according to stroboscopic information of the LED module during capturing the main image by the camera. The emotional tag corresponding to information of the black and white stripes is acquired by decoding the information of the black and white stripes of the photo, and the emotional tag is added to an original photo.

Further, in the practical application of adding the emotional tag according to the emotional state of the user described in the above arrangement, the user may have a usual emotion, which has little difference from the mood at ordinary times. The processing pressure of the system may be increased if the photographing processing is performed for the emotion of each moment. Accordingly, in an arrangement of the present disclosure, it may be selected whether to take a picture according to a current emotional state. Only when the user's emotional state is noteworthy, it is judged that the emotion is worthy to be recorded. Then a picture is taken and the emotional tag is added to the taken picture, which avoids wasting of resources and improves automation of photographing.

Specifically in this arrangement, a state threshold is preset, and the emotional state is compared with the preset state threshold after the emotional state of the user is evaluated according to the detected brain wave signal of the user. The emotional tag that labels the emotional state is acquired and the emotional tag is combined into the photo taken in the emotional state, responsive to obtaining that the emotional state is greater than or equal to the state threshold by the comparing. Photographing is stopped, responsive to obtaining that the emotional state is less than the state threshold by the comparing.

For example, a state threshold such as a degree of happy is set in advance, and responsive to the user's emotion exceeding the state threshold, the camera is automatically turned on. For example, when the user sees an interesting video, or encounters an interesting event on the street, and thus the degree of excitement reaches a certain value, in order to avoid missing the photographing time for recording, a static or dynamic image is directly captured by a camera module of a brain electricity product. At this time, the user may also choose to add his or her emotion to the captured image. The daily emotional fluctuations of the user are recorded along with the captured images, which is a better form of diary recording, and automates the photographing to avoid missing some meaningful moments in life.

It should be emphasized that the emotional tag recorded in the arrangement of the present disclosure may be an emotion description of the main image itself, or may be an emotional description of the user taking the photo who is not in the taken photo, which is dependent on the user from which the brain wave is detected.

For example, when a parent takes a picture of a child and the child is working on homework intently, the photo taken at this moment may show the child's normal form and further be attached with an emotional tag of "concentration". At this time, the emotional tag of "concentration" corresponds to the state of the child considered by the parent.

For another example, when a fan takes a photo of a star, the emotional tag of "excitement" attached to the photo does not represent the emotional state of the image, but the emotional state of the fan.

Based on the same principle, in an arrangement of the present disclosure, other manners may also be used to express the emotional state of the user. For example, an emotional audio file corresponding to the emotional state may be generated, and the emotional audio file may be combined into the photo taken in the emotional state. A pre-stored emotional audio file corresponding to the photo is played to express the emotion of the user responsive to detecting that the photo is opened.

For another example, color information corresponding to the emotional state may be generated, in which the sadder the color is closer to the cool color, and the happier the color is closer to the warm color, and the color information is combined into the photo taken in the emotional state. The pre-stored color information corresponding to the photo is displayed to reflect the user emotion responsive to detecting that the photo is opened, for example, a corresponding color pattern representing the emotion information is displayed in the upper right corner of the photo.

In summary, in the photographing processing method based on brain wave detection of the arrangement of the present disclosure, an emotional state of a user is evaluated according to a detected brain wave signal of the user, an emotional tag that labels the emotional state is obtained and the emotional tag is combined into a photo taken in the emotional state. Therefore, emotional information is added to the photo, which enriches the information content carried by the photo, and current emotion is directly recorded in the photo, which improves user experience.

It should be understood that in practical application, the user may only want the emotional state to be viewed by himself or a designated user. Therefore in this scene, the emotional tag is displayed in an invisible form in order to protect the privacy of the user.

Figure 4:
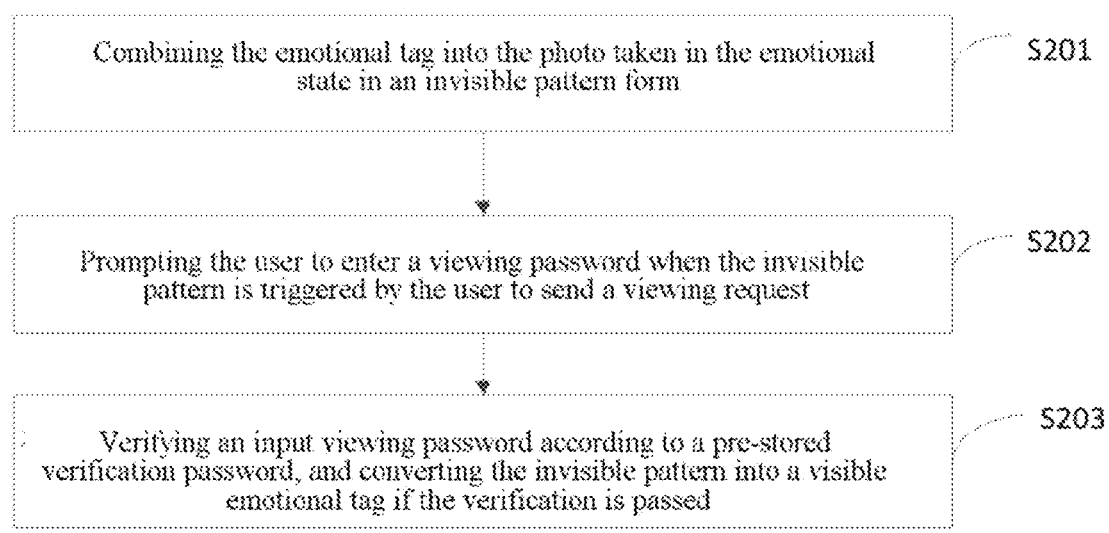
FIG. 4 is a flow chart of a photographing processing method based on brain wave detection according to a second arrangement of the present disclosure.

FIG. 4 is a flow chart of a photographing processing method based on brain wave detection according to a second arrangement of the present disclosure. As shown in FIG. 4, the combining the emotional tag into a photo taken in the emotional state in the above block S102 includes the following blocks.

In S201, the emotional tag is combined into the photo taken in the emotional state in an invisible pattern form.

The invisible pattern may be a pattern of a two-dimensional code, or some abstract pictures, or a stripe image formed by flashing of visible light in high frequency.

Specifically, the emotional tag is combined into a photo taken in a corresponding emotional state in an invisible pattern form, so that there is only one invisible pattern with unknown meaning in addition to the content of the photo itself viewed in the displayed photo, and the user cannot directly obtain emotional information from the photo.

In S202, the user is prompted to enter a viewing password responsive to determining the invisible pattern is triggered by the user to send a viewing request.

In S203, an input viewing password is verified according to a pre-stored verification password, and the invisible pattern is converted into a visible emotional tag responsive to passing the verification.

Specifically, responsive to the user triggering the invisible pattern, a viewing request is sent to prompt the user to input the viewing password. After the user inputs the viewing password, the input viewing password is verified according to the pre-stored verification password. Responsive to passing the verification, the invisible pattern is converted into a visible emotional tag so that the entire photo and the emotional tag mode will be displayed.

In different application scenes, the pre-stored verification password may be fingerprint information, password information, voice information, character information, gesture information, etc., which is not limited herein.

Figure 5:
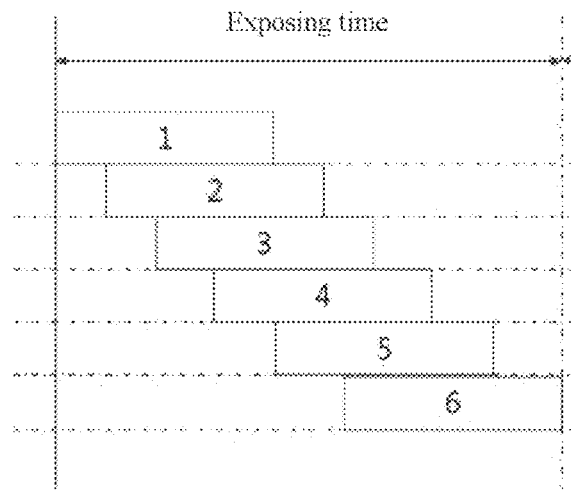
FIG. 5 is a schematic diagram of an application scene of a photographing processing method based on brain wave detection according to a specific arrangement of the present disclosure.

For example, if the invisible pattern is an invisible emotional coding pattern formed by flashing of visible light in high frequency, and a mobile phone is taken as an example for taking photo, since a rolling shutter is used in the photographing by the mobile phone, a photo is formed by progressive scanning as shown in FIG. 5, and the shutter frequency of the camera may reach several thousand k/s, character or pattern representing the emotion of the user at this time is encoded in real time to form a varying code stream of 0110001101 . . . , and then the LED of the brain wave detection device is driven to flash at a frequency of several thousand k/s, 1 represents bright, 0 represents dark. At this time, when taking a photo by the mobile phone, the mobile phone receives the brightness-changing information of the LED at the same time when a normal photo is formed by exposing in the mobile phone. Since the shutter matches the frequency of the LED, in the state of progressive exposure, a photo with non-obvious stripes is formed. When decoding is required, the information represented by the additional stripes in the photo can be decoded by the specific decoding program of the mobile phone.

Figure 6:
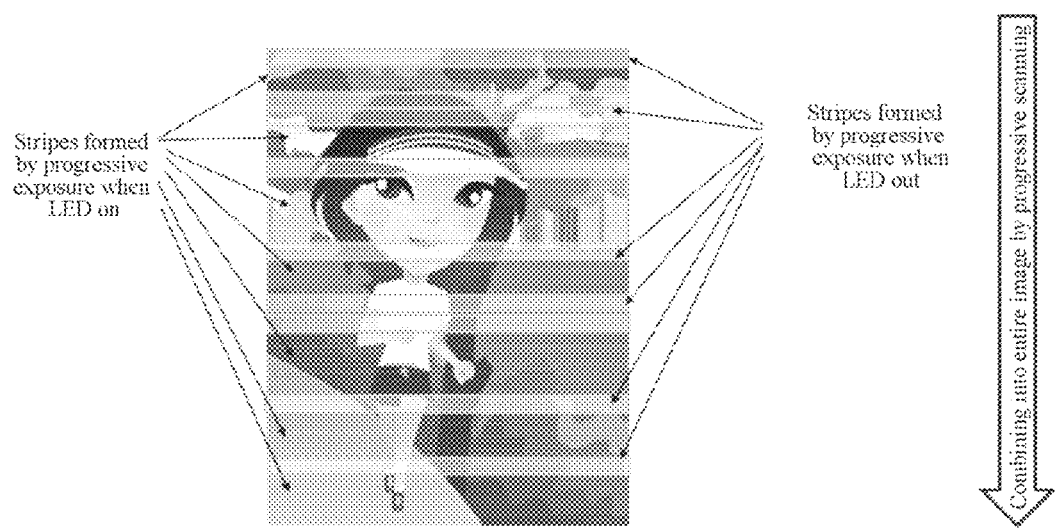
FIG. 6 is a schematic diagram of a photo with an invisible pattern according to a specific arrangement of the present disclosure.

A captured photo is shown in FIG. 6. It should be noted that FIG. 6 is only a schematic diagram, and actually, the width of the stripe is much narrower, and also there is a larger number of light and dark strips. Preferably, since the LED module needs to be photographed in emotional information receiving in visible light encryption, it is only available when taking a photo of oneself or taking a photo of a person with a brain wave detection device such as a headband.

In summary, in the photographing processing method based on brain wave detection of the arrangement of the present disclosure, the emotional tag is combined into the photo taken in the emotional state in an invisible pattern form, the user is prompted to enter a viewing password responsive to determining that the invisible pattern is triggered by the user to send a viewing request, and an input viewing password is verified according to a pre-stored verification password, and the invisible pattern is converted into a visible emotional tag responsive to determining that the verification is passed. Therefore, the emotional information of the user is protected, and the user experience is improved.

Based on the above arrangements, the user may store the emotional information in the photo in a log manner, and the emotional log may be shared between the users, so that the users can not only share the scene information seen by them, but also share the emotional information at that time.

Figure 7:
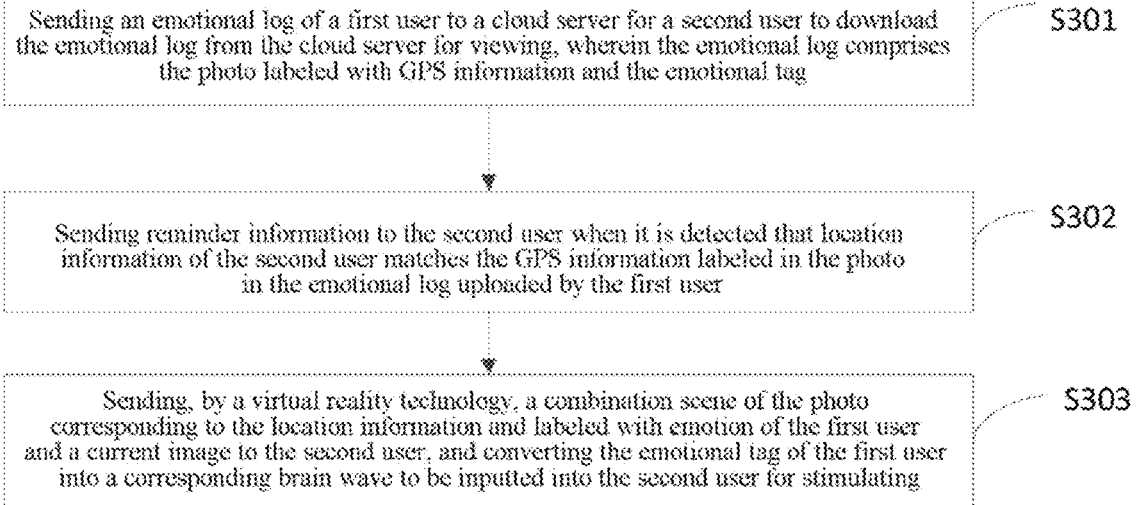
FIG. 7 is a flow chart of a photographing processing method based on brain wave detection according to a third arrangement of the present disclosure.

FIG. 7 is a flow chart of the photographing processing method based on brain wave detection according to a third arrangement of the present disclosure. As shown in FIG. 7, after the above block S102, the method further includes the following blocks.

In S301, an emotional log of a first user is sent to a cloud server for a second user to download the emotional log from the cloud server for viewing, wherein the emotional log includes the photo labeled with GPS information and the emotional tag.

Specifically, the users can share the emotional information. The user can upload an emotional diary to the cloud server in a specific form of a photo with the emotional information and the GPS information. The content of the photo can be a beautiful view that the user sees when traveling, or may be life bit by bit in the daily photographed by the user, so that the second user can view the emotional log of the first user by downloading the same from the cloud service, to get what the view is, what the mood is and what the place is.

In S302, reminder information is sent to the second user responsive to determining that location information of the second user matches the GPS information labeled in the photo in the emotional log uploaded by the first user.

Specifically, responsive to determining that location information of the second user matches the GPS information labeled in the photo in the emotional log uploaded by the first user, the reminder information is sent to the second user to remind the second user that the first user has also been at the location.

Depending on the specific application scene, the reminder information may be sent to the second user in different manners. For example, when the second user uses the mobile phone to take a photo, the reminder information is sent to the second user by sending a short message to the mobile phone or the like. For example, when the second user is taking a photo using a wearable bracelet, the reminder information is sent to the second user by vibrating the bracelet.

In S303, a combination scene of the photo corresponding to the location information and labeled with emotion of the first user and a current image is sent to the second user by a virtual reality technology, and the emotional tag of the first user is converted into a corresponding brain wave to be inputted into the second user for stimulating.

Specifically, when the second user comes to the same place as that in the photo uploaded by the first user, a combination scene of the photo corresponding to the location information and labeled with emotion of the first user and a current image is sent to the second user by a virtual reality technology, and the emotional tag of the first user is converted into a corresponding brain wave to be inputted into the second user for stimulating, so that the second user has a psychological effect of sharing the beautiful scenery with the first user.

It should be noted that, according to different application scenes, the emotional tag of the first user may be converted into a corresponding brain wave in different manners. As a possible implementation, the emotional tag of the first user is converted into the corresponding brain wave by a plurality of brain wave sensing metal electrodes disposed at different positions on an inner wall of a headband of the second user to be inputted to the second user for stimulating.

In order to make the present disclosure clearer to those skilled in the art, the present disclosure will be illustrated in conjunction with a specific application scene below.

In this example, the first user is represented by user 1, the second user is represented by user 2, and the user 2 uses actually downloaded photo that was uploaded by the user 1.

Figure 8:
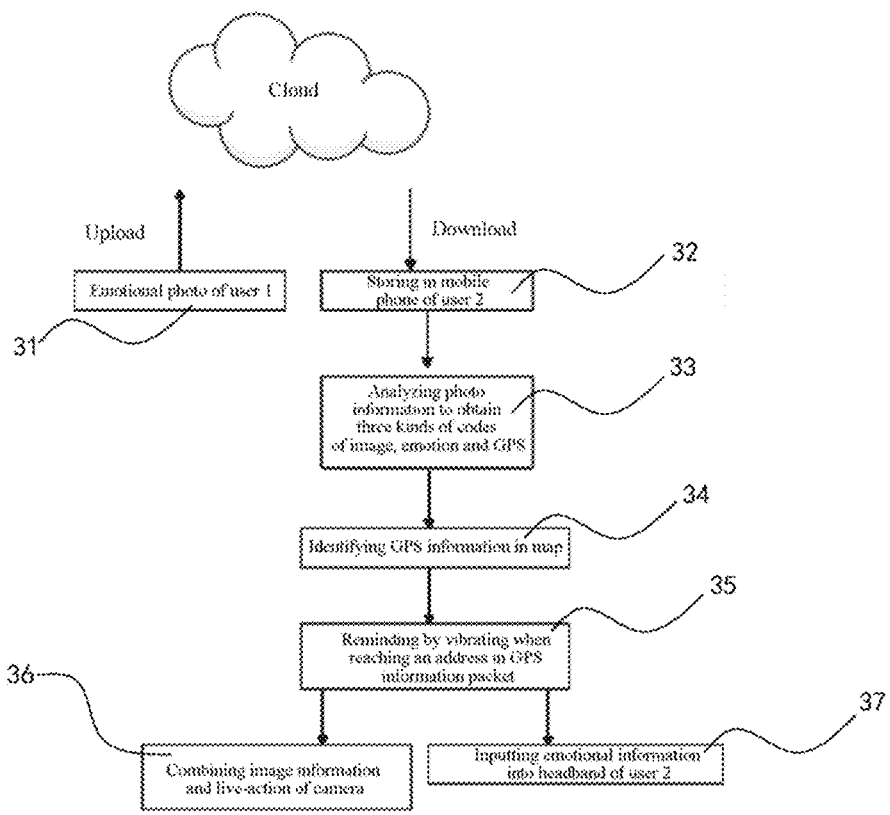
FIG. 8 is a schematic diagram of an application scene of a photographing processing method based on brain wave detection according to another specific arrangement of the present disclosure.

As shown in FIG. 8, when the user 1 and user 2 add each other as friends, they may share the contents of their emotional diaries. The user 2 can download the emotional log of the user 1, and after downloading, the user 2 can read the emotional log of the user 1 in a normal manner. 1 and can also set a special mode.

After downloading, all the GPS locations where the user 1 took the emotional photos are extracted. For example, the position information of one of the series of emotional photos of the user 1 is recorded as position 1. When the user 2 approaches this position, the brain electricity headband generates a vibration reminder, and at the same time, the mobile phone displays a specific prompt message, for example, that "you have reached a certain place of the Great Wall that somebody has visited". If the user turns on the mobile phone at this time and turns on the camera according to AR technology, the user can see the same image of the user 1 in the photo with enhanced display. At the same time, the brain wave acquires the waveform corresponding to the emotional photo, which gives the user 2 brain stimulation, so that the user 2 feels the emotion of the user 1 as much as possible, and achieves the psychological effect of sharing the beautiful scenery with the user 1.

In summary, in the photographing processing based on brain wave detection of the arrangement of the present disclosure, an emotional log of a first user is sent to a cloud server for a second user to download the emotional log from the cloud server for viewing, wherein the emotional log includes the photo labeled with GPS information and the emotional tag. Therefore, the sharing of the emotional log between the users is realized, which facilitates the sharing of the mood between the users in the same location, so that the users infect each other in mood across time, which has an important influence on the virtual reality.

Second Scene

In this scene, a tension state of a user is analyzed based on brain waves, and when the tension state reaches a certain level, an automatic alarming is activated for seeking help, which provides a new type of automatic alarming for help.

Figure 9:
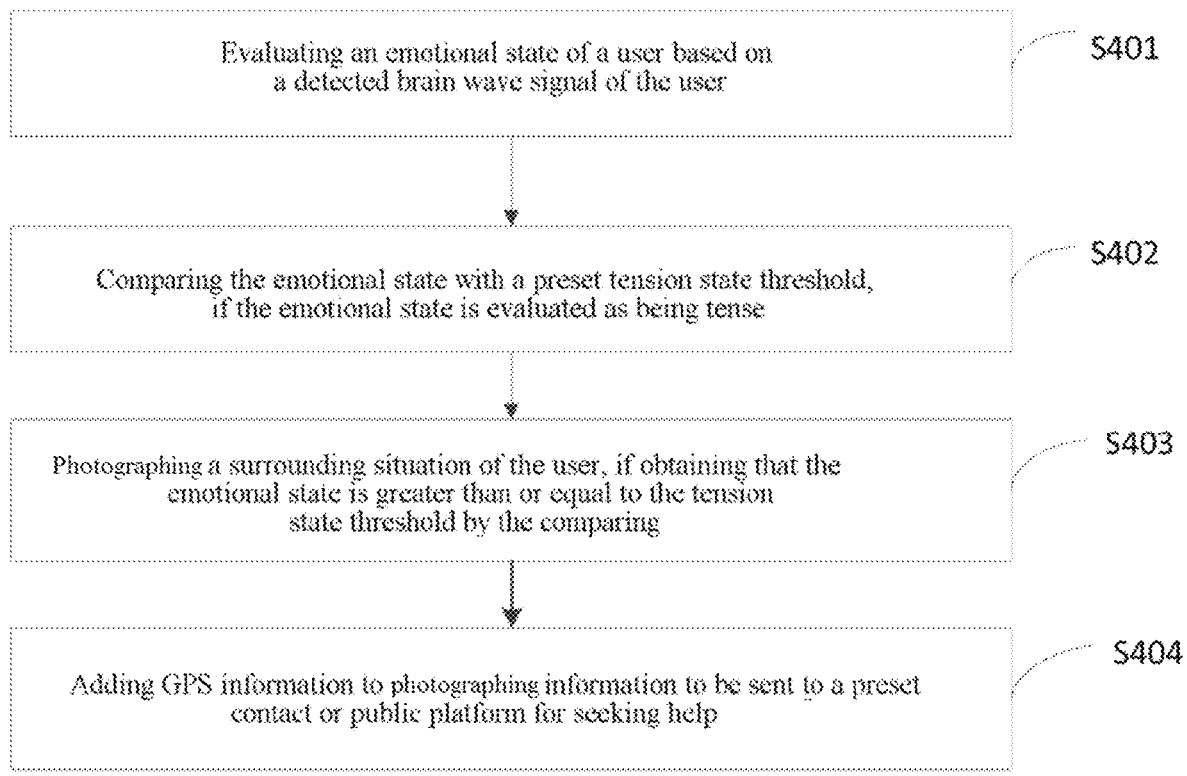
FIG. 9 is a flow chart of a photographing processing method based on brain wave detection according to a fourth arrangement of the present disclosure.

FIG. 9 is a flow chart of a photographing processing method based on brain wave detection according to a fourth arrangement of the present disclosure. As shown in FIG. 9, the method includes the following blocks.

In S401, an emotional state of a user is evaluated based on a detected brain wave signal of the user.

In S402, the emotional state is compared with a preset tension state threshold, responsive to evaluating that the emotional state is tense.

It can be understood that an emotional state of a user is evaluated according to a detected brain wave signal of the user. That is, as described above, the brain wave is some spontaneous rhythmic nerve electrical activity, which can be divided into $\alpha$ wave, $\beta$ wave, $\gamma$ wave and the like according to the frequency change thereof. Therefore, according to the different rhythm of nerve cell activity, the activity ranges of brain waves of different frequency bands are different, and based on this characteristic of the brain waves, the characteristics of brain waves of the user in a tension state are found.

Therefore, the detected brain wave signal is compared with the characteristics of the brain wave under the tension state, responsive to determining that the degree of matching is high, the emotional state is evaluated as being tense, and the emotional state is compared with the preset tension state threshold to determine whether the user is in a very tense state or not.

The tension state threshold is set in advance according to a large amount of experimental data, and generally the experimental data corresponds to a tension value when the user is in a very tense state to desire to call the police or seek help.

In S403, a surrounding situation of the user is shot, responsive to obtaining that the emotional state is greater than or equal to the tension state threshold by the comparing.

In S404, GPS information is added to photographing information to be sent to a preset terminal or server for seeking help.

Specifically, responsive to obtaining that the emotional state is greater than or equal to the tension state threshold by comparison, it is determined that the user may be in danger, such as when the user is coerced. Therefore, the camera is automatically turned on to photograph the surrounding situation of the user, and the GPS information is added to the photographing information to be sent to a preset terminal such as a mobile terminal (for example, a preset contact) or server or cloud (for example, a preset public platform) for seeking help.

It should be emphasized that in practical application, it is possible that even if the emotional state of the user is greater than the tension state threshold, it does not necessarily mean that the user desires to call the police or seek help. For example, when the user watches horror movies, sees shackles or the like, the fears may also cause the emotional state of the user to be greater than the tension state threshold. Therefore, in order to avoid false alarm and false help, the user may make confirmation before sending an alarm or asking for help.

For example, when the brain wave detection device is disposed in the headband, responsive to detecting that the emotional state of the user is greater than the tension state threshold, it delays for a certain time to call the police or ask for help, for example, delaying 5 s. A prompt voice is sent to the user through a bone conduction module preset on the headband, reply information of the user is detected through an acceleration sensor preset on the headband, the sending to the preset contact or the public platform is performed for seeking help, responsive to detecting that the user nods his head, and the sending to the preset contact or the public platform is cancelled, responsive to detecting that the user shakes his head.

Of course, in addition to the manner of the reply information of the user shown in the above example, the user can also reply in other ways, such as by voice reply or the like.

In summary, in the photographing processing method based on brain wave detection according to the arrangement of the present disclosure, an emotional state of a user is evaluated based on a detected brain wave signal of the user, the emotional state is compared with a preset tension state threshold responsive to evaluating that the emotional state is tense, a surrounding situation of the user is shot responsive to obtaining that the emotional state is greater than or equal to the tension state threshold by the comparing, and GPS information is added to photographing information to be sent to a preset contact or public platform for seeking help. Therefore, a new manner of alarming or seeking help is provided, which further improves the user experience and is of great significance to the user safety.

Third Scene

In this scene, the degree of interest of the user in goods such as clothing or the like when shopping is analyzed according to the brain wave, and when it is judged that the user is interested in the related product, the user is provided with information related to the product, thereby improving the shopping experience of the user.

In the arrangement of the present scene, for the convenience of description, it is illustrated by taking clothing as an example of goods.

Figure 10:
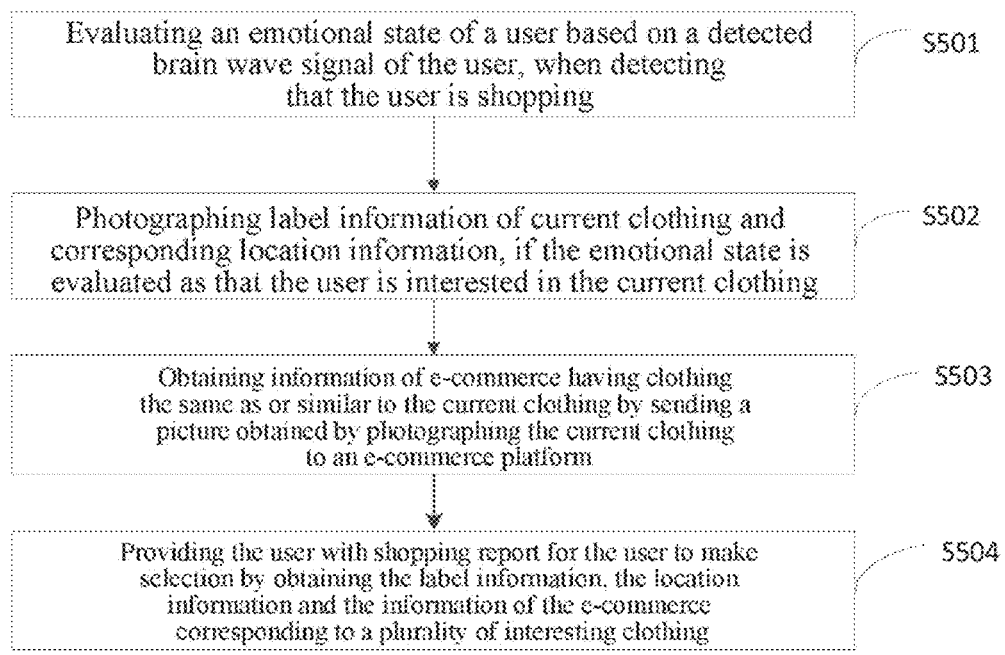
FIG. 10 is a flow chart of a photographing processing method based on brain wave detection according to a fifth arrangement of the present disclosure.

FIG. 10 is a flow chart of the photographing processing method based on brain wave detection according to a fifth arrangement of the present disclosure. As shown in FIG. 10, the method includes the following blocks.

In S501, an emotional state of a user is evaluated based on a detected brain wave signal of the user, responsive to detecting that the user is shopping.

It can be understood that an emotional state of a user is evaluated according to a detected brain wave signal of the user. That is, as described above, the brain wave is some spontaneous rhythmic nerve electrical activity, which can be divided into α wave, β wave, γ wave and the like according to the frequency change thereof. Therefore, according to the different rhythm of nerve cell activity, the activity ranges of brain waves of different frequency bands are different, and based on this characteristic of the brain waves, the characteristics of brain waves of the user when shopping are found.

Therefore, the detected brain wave signal is compared with the characteristics of the brain wave in the state of having interest, and responsive to determining that the degree of matching is high, the emotional state is evaluated as having interest.

In S502, label information of current clothing and corresponding location information are photographed, responsive to evaluating that the emotional state is that the user is interested in the current clothing.

Specifically, responsive to evaluating that the emotional state is that the user is interested in the current clothing, the label information of the current clothing and the corresponding location information are photographed.

It should be noted that, according to different application scenes, the label information of the current clothing may be photographed and the corresponding location information may be obtained in different manners. For example, if the user is currently using the mobile phone, the current clothing label information can be captured by triggering the photographing function of the headset connected to the mobile phone, and the GPS positioning information is obtained according to the positioning of the mobile phone. For another example, when the brain wave detection device is disposed in the headband, the camera and the positioning sensor on the headband can be used to capture the label information of the current clothing and obtain the corresponding position information. Of course, in this example, it can automatically take photos and get location information, or trigger the action for photographing photos and getting location information by blinking, nodding and the like, when it detects that the user is very interested in a certain product.

In S503, information of e-commerce having clothing the same as or similar to the current clothing is obtained by sending a picture obtained by photographing the current clothing to an e-commerce platform.

In S504, the user is provided with shopping report for the user to make selection by obtaining the label information, the location information and the information of the e-commerce corresponding to a plurality of interesting clothing.

Specifically, information of e-commerce having clothing the same as or similar to the current clothing is obtained by sending a picture obtained by photographing the current clothing to an e-commerce platform, and then the user is provided with shopping report for the user to make selection by obtaining the label information, the location information and the information of the e-commerce corresponding to a plurality of interesting clothing, which greatly improves the user shopping experience.

In order to make the workflow of the photographing processing method based on brain wave detection in the present arrangement clearer to those skilled in the art, it is illustrated below in conjunction with a specific application scene.

In this example, the photographing function of the headset can be used to assist the user in daily shopping. Responsive to detecting that the user is located in a shopping mall or supermarket in conjunction with GPS positioning, it is automatically switched to a shopping mode. In this mode, it focuses on analyzing whether the user is interested in a certain product by monitoring the brain wave signal.

In most cases, women in shopping malls need to constantly compare various clothes that they like and then make final selection among them. For example, when we see clothing A and like it, it is detected that the brain wave signal is changed at this time, the photographing function is automatically activated to photograph the clothing, and at the same time, it is associated with Taobao or other e-commerce platform. After the image recognition is performed on the photographed clothing, it searches for the clothing of same or similar kind in the database of the e-commerce platform, and then the results are pushed to the mobile phone of the user. Because the same clothes on the e-commerce platform are often much cheaper than the physical store, it is convenient for users to make more cost-effective selection. If the user does not immediately decide whether to buy the clothing or not, the clothing tag may be recorded through the brain electricity headband, so that the trademark and price of the clothing are recorded through image recognition, and at the same time, the location of this clothing is recorded in conjunction with an indoor positioning system.

Figure 11:
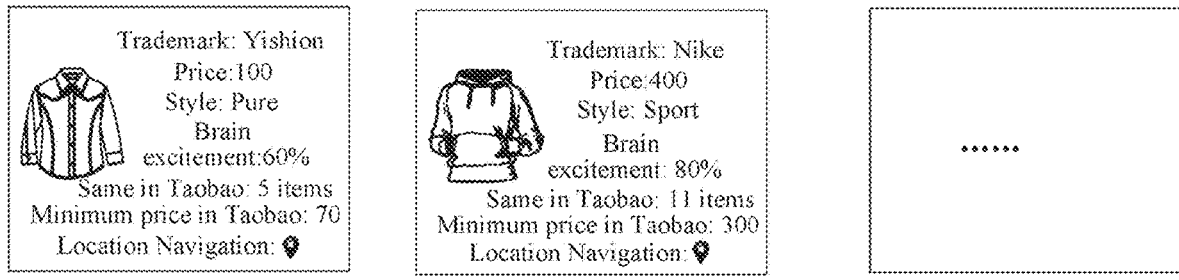
FIG. 11 is a schematic diagram of an application scene of a photographing processing method based on brain wave detection according to still another specific arrangement of the present disclosure.

If the user continues to choose clothing, for example, the user feels that clothing B looks good, the same process is repeated. Finally, a shopping report is generated in real time on the mobile phone, as shown in FIG. 11, specifically, referring to reference numerals 41 and 42 shown in FIG. 11, which includes trademark, style, price of the alternative clothing and that of the same or similar clothing found in the e-commerce platform, so that the user does not have to remember the price, appearance and location of each piece of clothing, and can make a more intuitive choice through the report.

In summary, in the photographing processing method based on brain wave detection of the arrangement of the present disclosure, an emotional state of a user is evaluated based on a detected brain wave signal of the user responsive to detecting that the user is shopping, label information of current clothing and corresponding location information is photographed responsive to evaluating that the emotional state is that the user is interested in the current clothing, information of e-commerce having clothing the same as or similar to the current clothing is obtained by sending a picture obtained by photographing the current clothing to an e-commerce platform, the user is provided with shopping report for the user to make selection by obtaining the label information, the location information and the information of the e-commerce corresponding to a plurality of interesting clothing. Therefore, the convenience of the user shopping is greatly facilitated, and the shopping experience of the user is improved.

Fourth Scene

In this scene, the user's interest in the advertisement is analyzed according to the brain wave, and if the user is interested in the related advertisement, the user is provided with the purchase link of the corresponding product of the advertisement. On the one hand, it improves the attraction of advertisement, on the other hand, it facilitates the purchase behavior of the user.

Figure 12:
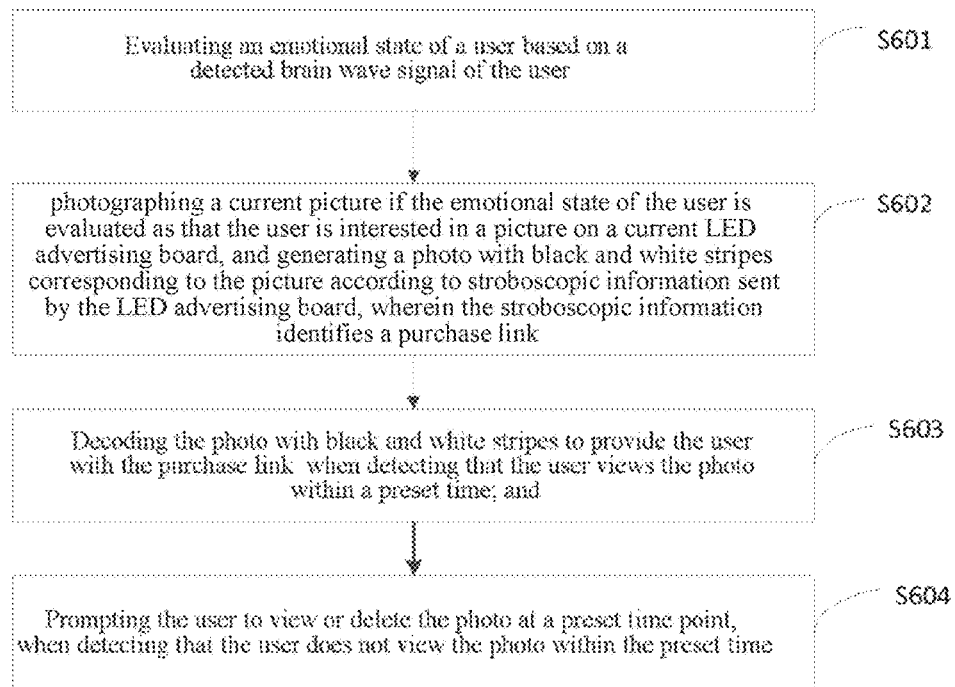
FIG. 12 is a flow chart of a photographing processing method based on brain wave detection according to a sixth arrangement of the present disclosure.

FIG. 12 is a flow chart of a photographing processing method based on brain wave detection according to a sixth arrangement of the present disclosure. As shown in FIG. 12, the method includes the following blocks.

In S601, an emotional state of a user is evaluated based on a detected brain wave signal of the user.

It can be understood that an emotional state of a user is evaluated according to a detected brain wave signal of the user. That is, as described above, the brain wave is some spontaneous rhythmic nerve electrical activity, which can be divided into α wave, β wave γ wave and the like according to the frequency change thereof. Therefore, according to the different rhythm of nerve cell activity, the activity ranges of brain waves of different frequency bands are different, and based on this characteristic of the brain waves, the characteristics of brain waves of the user when the user is shopping and interested in some goods are found.

Therefore, the detected brain wave signal is compared with the characteristics of the brain wave in the state of having interest, and responsive to determining that the degree of matching is high, the emotional state is evaluated as having interest.

In S602, a current picture is photographed responsive to evaluating that the emotional state of the user is that the user is interested in a picture on a current LED advertising board, and a photo with black and white stripes corresponding to the picture is generated according to stroboscopic information sent by the LED advertising board, wherein the stroboscopic information identifies a purchase link.

It can be understood that in the present example, a visible light communication is combined, and the visible light communication has been applied to a public advertising board. In order to attract users, the LED advertising board is mainly based on large-size images, and the purchase method of the products is sent by forming data stream through the high-speed strobe LED.

Specifically, a current picture is photographed responsive to evaluating that the emotional state of the user is that the user is interested in a picture on a current LED advertising board, and a photo with black and white stripes corresponding to the picture is generated according to stroboscopic information sent by the LED advertising board, wherein the stroboscopic information identifies a purchase link.

For example, if the user is currently using the mobile phone, the LED advertising board can be captured by triggering the photographing function of the headset connected to the mobile phone. For another example, when the brain wave detection device is disposed in the headband, the camera on the headband can be used to capture the LED advertising board. Of course, in this example, it can automatically take photos of the LED advertising board, or trigger the action of taking photos of the LED advertising board by blinking, nodding and the like, when it detects that the user is very interested in a certain product.

In S603, the photo with black and white stripes is decoded to provide the user with the purchase link responsive to determining that that the user views the photo within a preset time.

In S604, the user is prompted to view or delete the photo at a preset time point, responsive to determining that that the user does not view the photo within the preset time.

Specifically, the photo with black and white stripes is decoded to provide the user with the purchase link responsive to determining that that the user views the photo within a preset time such as 3 minutes; the user is prompted to view or delete the photo at a preset time point, responsive to determining that that the user does not view the photo within the preset time, in order to avoid memory occupying.

In order to make the workflow of the photographing processing method based on brain wave detection in the present arrangement clearer to those skilled in the art, it is illustrated below in conjunction with a specific application scene.

The traditional way is that when the user sees the advertising board and feels that the product is worth buying, the user turns on the camera of the mobile phone for photographing, and thus the code stream formed by the strobe of the LED is received, and striped photo recording the code stream of the purchase mode is formed, and then it is decoded and jumped to the corresponding purchase website.

Figure 13:
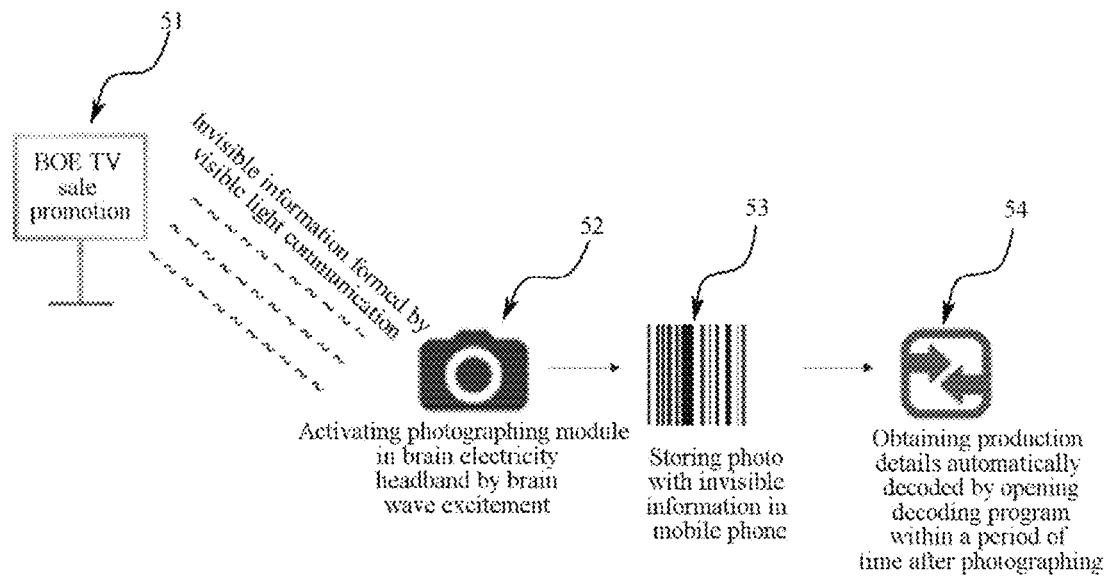
FIG. 13 is a schematic diagram of an application scene of a photographing processing method based on brain wave detection according to still another specific arrangement of the present disclosure.

In the present arrangement, as shown in FIG. 13, specifically, referring to reference numerals 51-54 shown in FIG. 13, combined with brainwave detection equipment such as headbands, it can detect whether the user is interested in products in the advertising board by detecting changes in brainwave signals at any time, responsive to determining that that the user is interested in this product, the photographing function is activated, and the purchase link of the product is automatically recorded in the form of a photo, and the purchase link is stored in the form of a photo in a terminal device such as a mobile phone. When the user opens the corresponding program within a certain period of time, such as 3 minutes, it indicates that the user wants to see the detailed purchase information of the product at this time, then the photo is automatically decoded responsive to the user opening the program, and simultaneously the detailed purchase information is displayed. Responsive to determining that the user does not open the corresponding program after a certain period of time after taking the photo, it means that the user does not have time at this time or feels that it is unnecessary to read the product details, and the photos are also stored, when the user opens the corresponding program later, the user is prompted to view the product purchase details or delete the photos storing the product details. It eliminates the trouble of the user pulling out the terminal device such as the mobile phone, and can accurately record the user preference according to the user real reaction, and store it for the user to view later.

In summary, in the photographing processing method based on brain wave detection of the arrangement of the present disclosure, an emotional state of a user is evaluated based on a detected brain wave signal of the user; a current picture is photographed responsive to evaluating that the emotional state of the user is that the user is interested in a picture on a current LED advertising board, and a photo with black and white stripes corresponding to the picture is generated according to stroboscopic information sent by the LED advertising board; the photo with black and white stripes is decoded to provide the user with the purchase link responsive to detecting that the user views the photo within a preset time; and the user is prompted to view or delete the photo at a preset time point, responsive to detecting that the user does not view the photo within the preset time. Therefore, the promotion efficiency of the advertisement is improved, and the purchase behavior of the user is facilitated.

Based on the above arrangements, it should be emphasized that the foregoing arrangements only show that when the brain wave signal is changed correspondingly according to the visual stimulus, the related operation is performed. In the actual execution process, the stimulus may be felt by hearing in addition to seeing. For example, also, when something interesting or a moving piece of music is heard, a recording mode may be open for recording according to the change of the brain wave signal. In addition, if the brain electricity analysis shows that the user very like a certain piece of music at a certain moment, the music is recognized by a speech recognition module to be transmitted to a central processor for music recognition and record the name of the music, so that the user can find the favorite music. No whether it is auditory stimulation or speech stimulation, the implementation principle of related operations combined with changes in brain wave signals is same as the visual stimulation, which will not be described herein.

Figure 14:
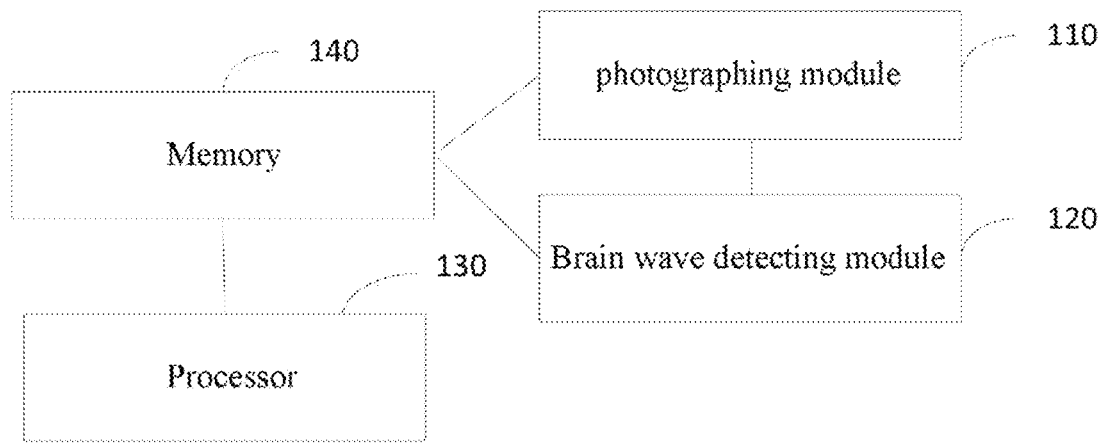
FIG. 14 is a schematic structural diagram of a wearable device for photographing based on brain wave detection according to a first arrangement of the present disclosure.

In order to implement the above arrangements, the present disclosure also provides a wearable device for photographing based on brain wave detection. FIG. 14 is a schematic structural view of a wearable device for photographing based on brain wave detection according to the first arrangement of the present disclosure, as shown in FIG. 14, the wearable device for photographing based on brain wave detection includes: a photographing module 110, a brain wave detecting module 120, a processor 130, and a memory 140, wherein the memory 140 is connected to the photographing module 110 and the brain wave detecting module 120, and the processor 130, by reading an executable program code stored in the memory 140, executes a program corresponding to the executable program code for implementing the photographing processing method based on brain wave detection as described in the first scene.

Figure 15:
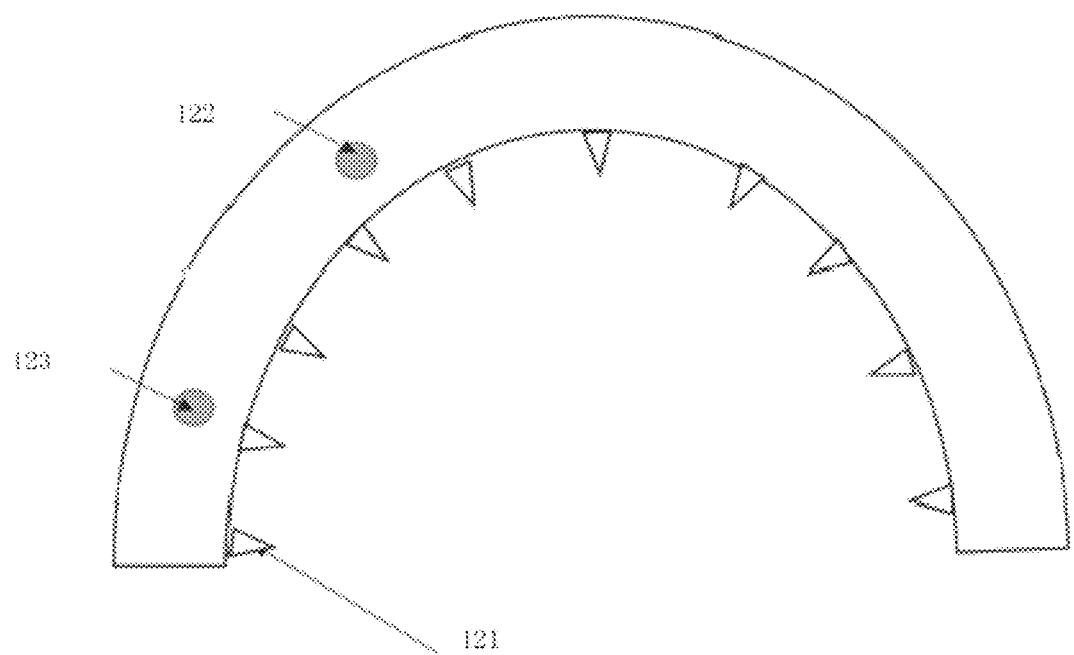
FIG. 15 is a schematic structural diagram of a headband according to an arrangement of the present disclosure.

In an arrangement of the present disclosure, when the wearable device is a headband, as shown in FIG. 15, the headband includes a plurality of brain wave sensing metal electrodes 121 at different positions on an inner wall of a headband, wherein the plurality of brain wave sensing metal electrodes 121 are configured to detect a brain wave signal of the user. Referring to FIG. 15, the headband further includes a light emitting diode (LED) module 122, which is configured to perform strobe according to an encoded code stream, wherein the encoded code stream is obtained by encoding the emotional state.

With continued reference to FIG. 15, the headband may further include a wireless communication module 123, which is configured to send an emotional log of a first user to a cloud server for a second user to download the emotional log from the cloud server for viewing, wherein the emotional log includes a photo labeled with GPS information and the emotional tag.

It should be noted that, the explanation of the photographing processing method based on the brain wave detection in the first scene is also applicable to the wearable device for photographing based on the brain wave detection of the arrangement of the present disclosure, and the implementation principle and the technical effect are similar, which will not be repeated herein.

Figure 16:
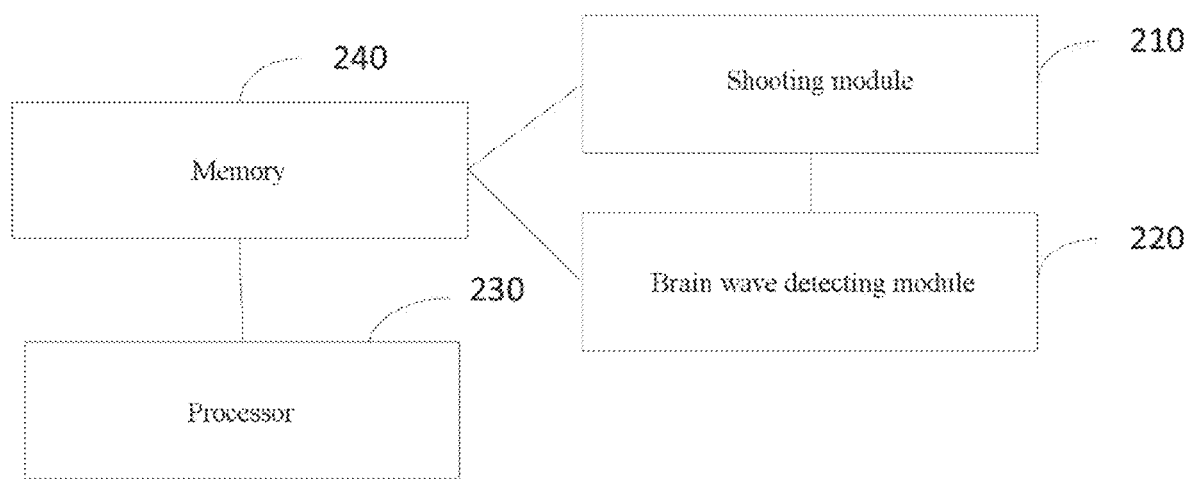
FIG. 16 is a schematic structural diagram of a wearable device for photographing based on brain wave detection according to a second arrangement of the present disclosure.

In order to implement the above arrangements, the present disclosure also provides a wearable device for photographing based on brain wave detection. FIG. 16 is a schematic structural view of a wearable device for photographing based on brain wave detection according to the second arrangement of the present disclosure, as shown in FIG. 16, the wearable device for photographing based on brain wave detection includes: a photographing module 210, a brain wave detecting module 220, a processor 230, and a memory 240, wherein the memory 240 is connected to the photographing module 210 and the brain wave detecting module 220, and the processor 230, by reading an executable program code stored in the memory 240, executes a program corresponding to the executable program code for implementing the photographing processing method based on brain wave detection as described in the second scene.

Figure 17:
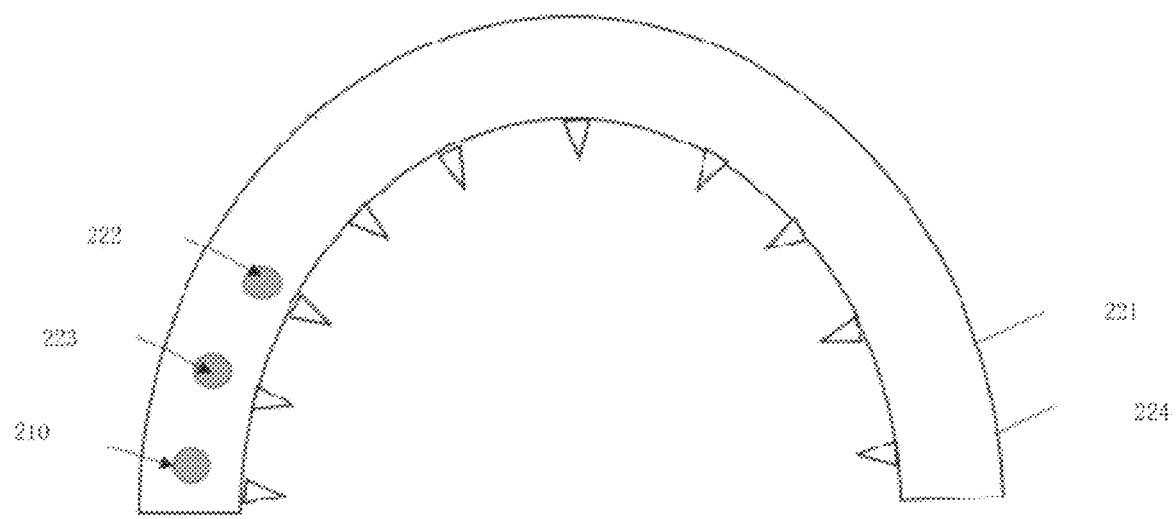
FIG. 17 is a schematic structural diagram of a headband according to another arrangement of the present disclosure.

In an arrangement of the present disclosure, when the wearable device is a headband, as shown in FIG. 17, the headband includes a bone conduction module 221, an acceleration sensor 222, and a wireless communication module 223.

The bone conduction module 221 is preset on the headband for sending a prompt voice to a user.

The acceleration sensor 222 is configured to detect reply information of the user.

The wireless communication module 223 is configured to perform sending to a preset contact or a public platform for seeking help responsive to detecting that the user nods his head, and to cancel the sending to a preset contact or a public platform responsive to detecting that the user shakes his head.

As shown in FIG. 17, the photographing module 210 can also be disposed in the headband, and the position of the photographing module 210 is at the same level as the user eyes, so as to accurately record the image observed by the user eyes.

Of course, as shown in FIG. 17, the voice recognition module 224 and the like may also be included in the headband device according to the needs of the function, which is not limited herein.

It should be noted that, the explanation of the photographing processing method based on the brain wave detection in the second scene is also applicable to the wearable device for photographing based on the brain wave detection of the arrangement of the present disclosure, and the implementation principle and the technical effect are similar, which will not be repeated herein.

Figure 18:
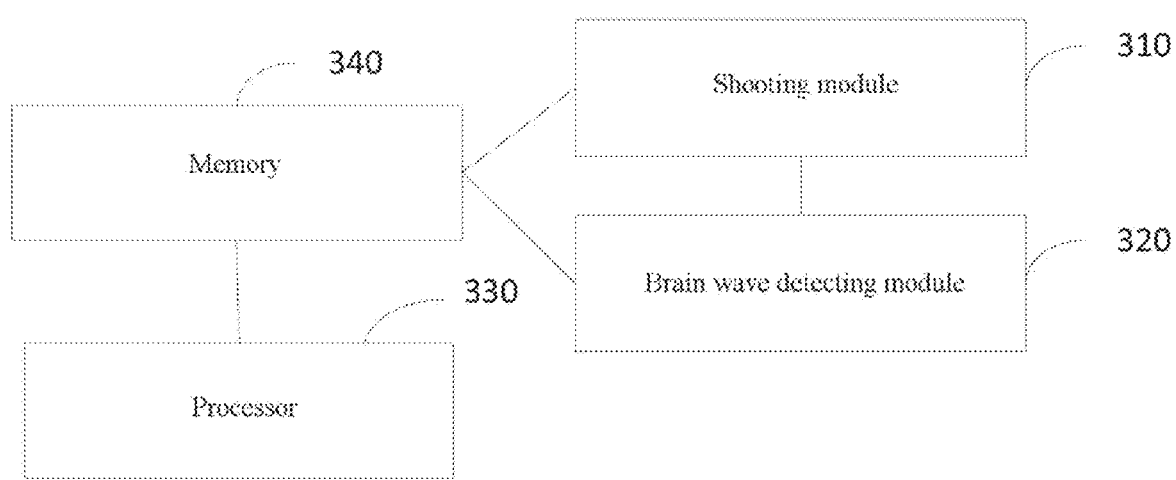
FIG. 18 is a schematic structural diagram of a wearable device for photographing based on brain wave detection according to a third arrangement of the present disclosure.

In order to implement the above arrangements, the present disclosure also provides a wearable device for photographing based on brain wave detection. FIG. 18 is a schematic structural view of a wearable device for photographing based on brain wave detection according to the second arrangement of the present disclosure, as shown in FIG. 18, the wearable device for photographing based on brain wave detection includes: a photographing module 310, a brain wave detecting module 320, a processor 330, and a memory 340, wherein the memory 340 is connected to the photographing module 310 and the brain wave detecting module 320, and the processor 330, by reading an executable program code stored in the memory 340, executes a program corresponding to the executable program code for implementing the photographing processing method based on brain wave detection as described in the third scene.

It should be noted that, the explanation of the photographing processing method based on the brain wave detection in the third scene is also applicable to the wearable device for photographing based on the brain wave detection of the arrangement of the present disclosure, and the implementation principle and the technical effect are similar, which will not be repeated herein.

Figure 19:
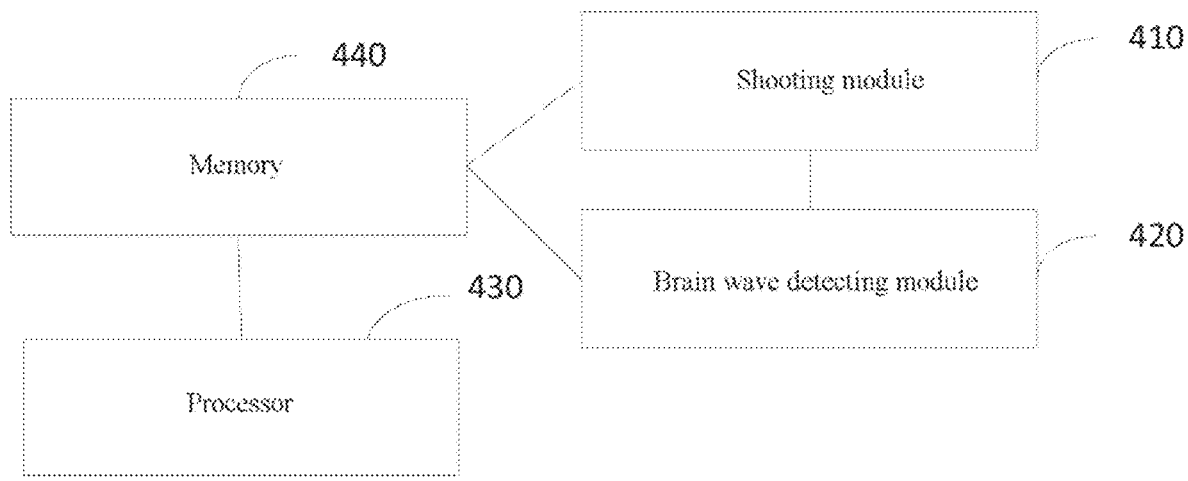
FIG. 19 is a schematic structural diagram of a wearable device for photographing based on brain wave detection according to a fourth arrangement of the present disclosure.

In order to implement the above arrangements, the present disclosure also provides a wearable device for photographing based on brain wave detection. FIG. 19 is a schematic structural view of a wearable device for photographing based on brain wave detection according to the fourth arrangement of the present disclosure, as shown in FIG. 19, the wearable device for photographing based on brain wave detection includes: a photographing module 410, a brain wave detecting module 420, a processor 430, and a memory 440, wherein the memory 440 is connected to the photographing module 410 and the brain wave detecting module 420, and the processor 430, by reading an executable program code stored in the memory 440, executes a program corresponding to the executable program code for implementing the photographing processing method based on brain wave detection as described in the fourth scene.

It should be noted that, the explanation of the photographing processing method based on the brain wave detection in the fourth scene is also applicable to the wearable device for photographing based on the brain wave detection of the arrangement of the present disclosure, and the implementation principle and the technical effect are similar, which will not be repeated herein.

Figure 20:
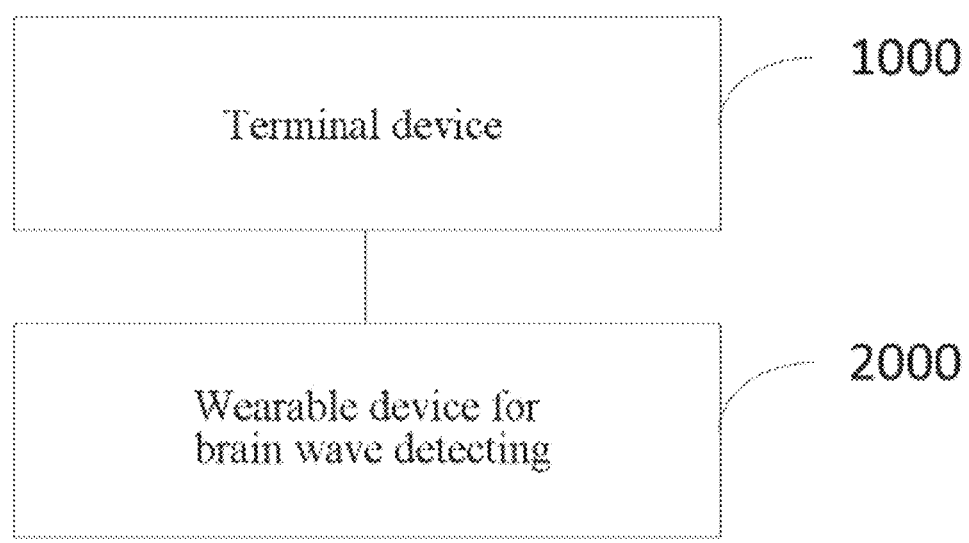
FIG. 20 is a schematic structural diagram of a photographing system based on brain wave detection according to a first arrangement of the present disclosure.

In order to implement the above arrangements, the present disclosure also provides a photographing system based on brain wave detection. FIG. 20 is a schematic structural diagram of a photographing system based on brain wave detection according to the first arrangement of the present disclosure, and as shown in FIG. 20, the system includes: a terminal device 1000 having a photographing module, and a wearable device 2000 for brain wave detecting, wherein the wearable device 2000 for brain wave detecting is configured to detect a brain wave signal of the user.

The terminal device 1000 is configured to implement the photographing processing method based on brain wave detection described in the first scene.

Figure 21:
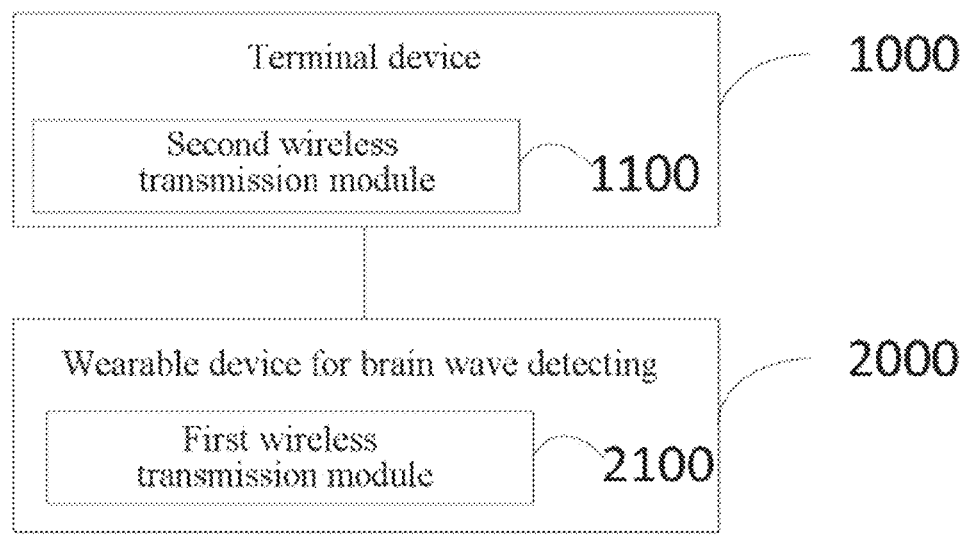
FIG. 21 is a schematic structural diagram of a photographing system based on brain wave detection according to a second arrangement of the present disclosure.

In an arrangement of the present disclosure, FIG. 21 shows a schematic structural diagram of a photographing system based on brain wave detection according to a second arrangement of the present disclosure, from which it can be seen that on the basis of what shown in FIG. 20, the wearable device 2000 for brain wave detecting includes a first wireless transmission module 2100, the terminal device 1000 includes a second wireless transmission module 1100, the first wireless transmission module 2100 is configured to send the detected brain wave signal of the user to the second wireless transmission module 1100 of the terminal device 1000.

In order to make those skilled in the art understand more clearly, in this arrangement, the work flow of the photographing system based on brain wave detection is described below by taking the mobile phone as an example of the terminal device and the headband as an example of the wearable device.

Figure 22A:
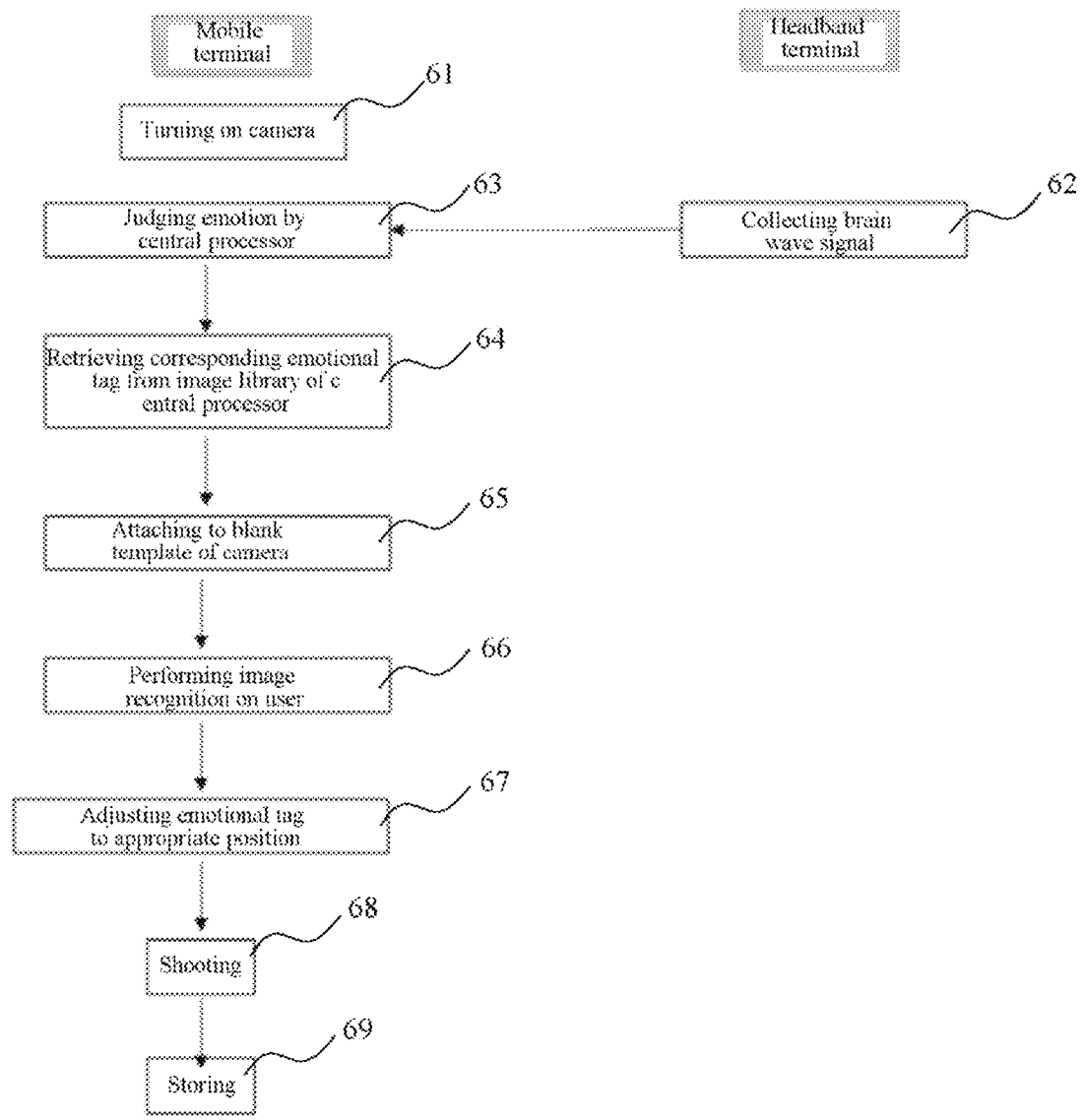
FIG. 22(a) is a schematic diagram of an application scene of a photographing system based on brain wave detection according to a first arrangement of the present disclosure.

As shown in FIG. 22(a), specifically, referring to reference numerals 61-69 shown in FIG. 22(a), the headband collects the brain wave signal of the user and sends the same to the mobile phone, the camera of the mobile phone is turned on to take a photo, and the central processor in the mobile phone judges the user's emotion. Then the emotional tag corresponding to the brain wave signal is retrieved from the image library of the central processor, and is attached to the blank template of the camera. Then, the main image is recognized and the emotional tag is adjusted to an appropriate position, and thus a photo with the emotional tag is generated and stored.

Figure 22B:
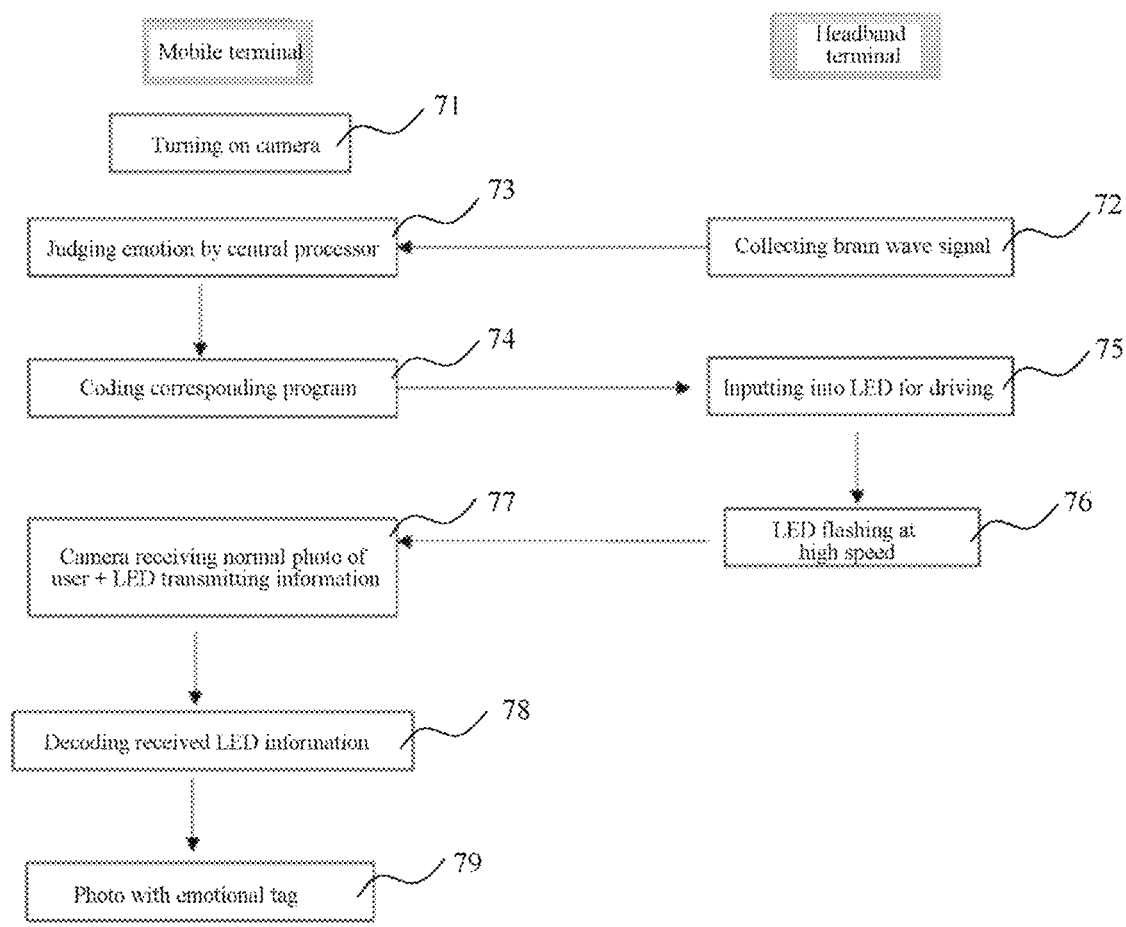
FIG. 22(b) is a schematic diagram showing an application scene of a photographing system based on brain wave detection according to a second arrangement of the present disclosure.

As shown in FIG. 22(b), specifically, referring to reference numerals 71-79 shown in FIG. 22(b), the headband collects the brain wave signal of the user and sends the same to the mobile phone, the camera of the mobile phone is turned on to take a photo, and the central processor in the mobile phone judges the user's emotion. Then the emotional tag corresponding to the brain wave signal is retrieved from the image library of the central processor, and the corresponding coded code stream is sent to the LED driving module of the headband, so that the LED driving module controls the LED lamp to flash at high speed. Further, the camera in the mobile phone receives the photo normally taken by the user and the information transmitted from LED, the received LED information is decoded, and a photo with the emotional tag is generated.

Figure 22C:
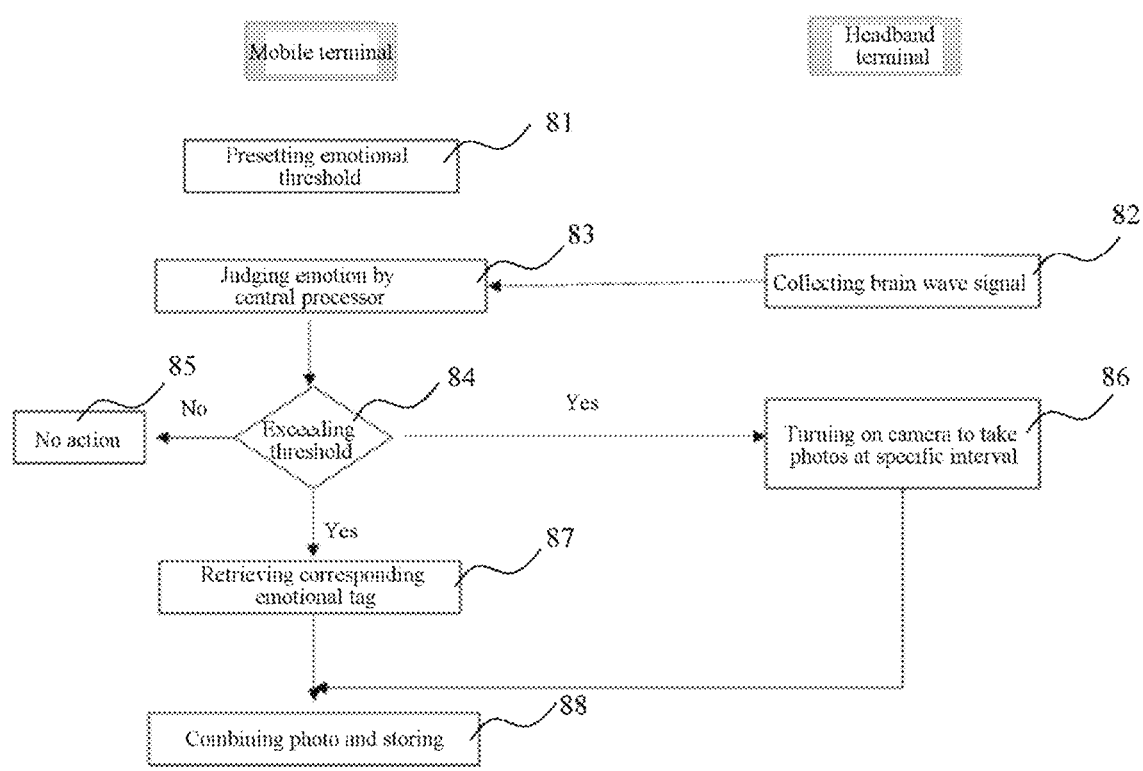
FIG. 22(c) is a schematic diagram showing an application scene of a photographing system based on brain wave detection according to a third arrangement of the present disclosure.

As shown in FIG. 22(c), specifically, referring to reference numerals 81-88 shown in FIG. 22(c), the mobile terminal stores a preset emotional state threshold, and after the brain wave signal of the user detected by the headband is acquired, the central processor of the mobile phone determines the current emotional state, and determines whether it exceeds the emotional state threshold according to the emotional state. responsive to determining that it does not exceed the emotional state threshold, the related action is not activated, and responsive to determining that it exceeds the emotional state threshold, the camera is turned on to take photos at a specific interval. The corresponding emotional tag is retrieved at the same time, and the emotional tag and the photo at the corresponding time are combined and stored.

Figure 22D:
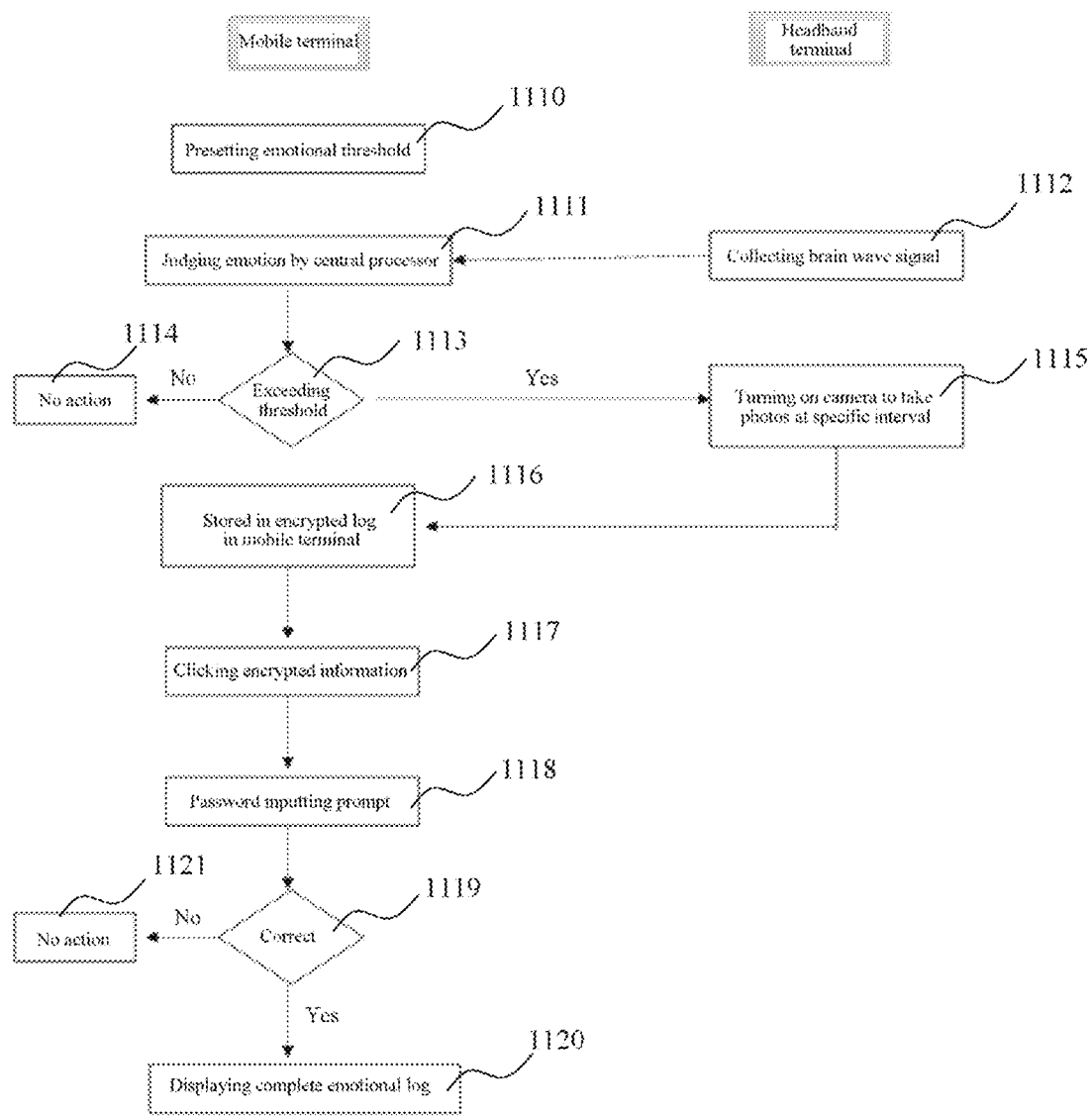
FIG. 22(d) is a schematic diagram showing an application scene of a photographing system based on brain wave detection according to a fourth arrangement of the present disclosure.

As shown in FIG. 22(d), specifically, referring to reference numerals 1110-1121 shown in FIG. 22(d), the preset emotion threshold is stored in the mobile phone, and the brain wave signal collected by the headband is acquired. The central processor in the mobile phone determines whether the user's emotional state exceeds the emotion threshold according to the detected brain wave signal. Responsive to determining that it does not exceed the emotion threshold, there is no action. Responsive to determining that it exceeds the emotion threshold, the camera is turned on to perform detection and take photos at a specific time, and the photos are stored in the encrypted form in the mobile phone to form an encrypted log. When the user clicks the encrypted picture, the user is prompted to enter password. The complete emotional log is displayed to the user only when the password is entered correctly.

Figure 23:
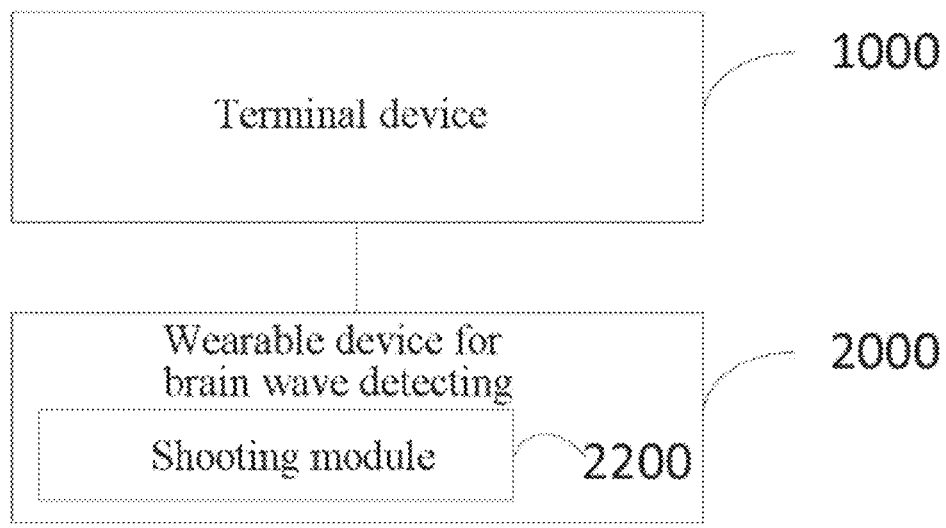
FIG. 23 is a schematic structural diagram of a photographing system based on brain wave detection according to a third arrangement of the present disclosure.

Of course, in an arrangement of the present disclosure, FIG. 23 shows a schematic structural diagram of the photographing system based on the brain wave detection according to the third arrangement of the present disclosure, from which it can be seen that, on the basis of what shown in FIG. 20, the wearable device 2000 for brain wave detection further includes a photographing module 2200, so that analysis of emotions and photographing are integrated in the wearable device 2000 for brain wave detection, which simplifies the structure of the photographing system based on the brain wave detection, and improves the usability.

It should be noted that, the explanation of the photographing processing method based on the brain wave detection in the first scene is also applicable to the photographing system based on the brain wave detection of the arrangement of the present disclosure, and the implementation principle and the technical effect are similar, which will not be repeated herein.

Figure 24:
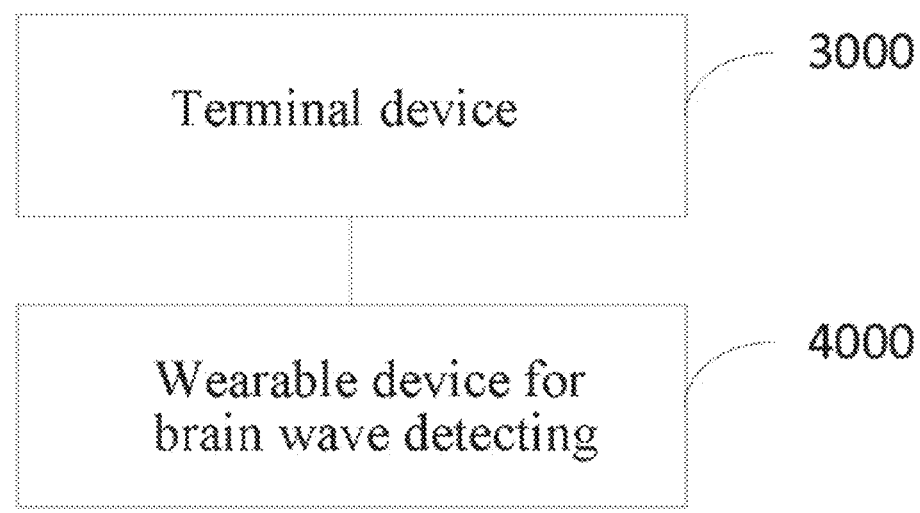
FIG. 24 is a schematic structural diagram of a photographing system based on brain wave detection according to a fourth arrangement of the present disclosure.

In order to implement the above arrangements, the present disclosure also provides a photographing system based on brain wave detection. FIG. 24 is a schematic structural diagram of a photographing system based on brain wave detection according to the fourth arrangement of the present disclosure, and as shown in FIG. 24, the system includes a terminal device 3000 having a photographing module, and a wearable device 4000 for brain wave detecting, wherein the wearable device 4000 for brain wave detecting is configured to detect a brain wave signal of the user.

The terminal device 3000 is configured to implement the photographing processing method based on brain wave detection described in the second scene.

In order to make those skilled in the art understand more clearly, in this arrangement, the work flow of the photographing system based on brain wave detection is described below by taking the mobile phone as an example of the terminal device and the headband as an example of the wearable device.

Figure 25:
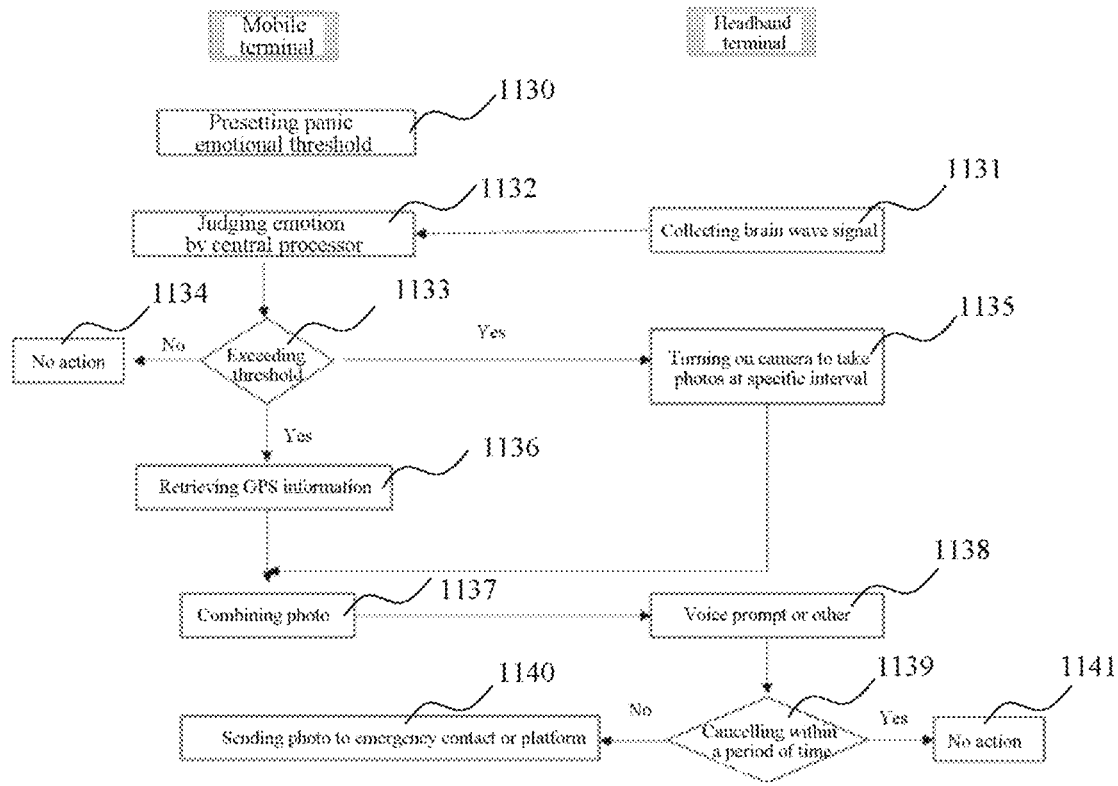
FIG. 25 is a schematic diagram of an application scene of a photographing system based on brain wave detection according to a fifth arrangement of the present disclosure.

As shown in FIG. 25, specifically, referring to reference numerals 1130-1141 shown in FIG. 25, a preset panic emotion threshold is stored in the mobile phone. Further, the brain wave information collected by the headband is acquired, and the central processor determines whether the user's emotion exceeds the emotional state threshold. If it is not, there is no the action performed. If it is yes, the camera is turned on to perform detection and take a photo at a specific time. The current GPS information is retrieved at the same time, and the GPS information is added to the corresponding photo to form a combined photo. Further, the user is prompted to call the police or seeking help by voice or in other means. When the user takes action of cancelling within a certain period of time, the calling police or seeking help is cancelled. When there is no action of cancelling, the alarm information is sent to the emergency contact or the help platform.

It should be noted that, the explanation of the photographing processing method based on the brain wave detection in the second scene is also applicable to the photographing system based on the brain wave detection of the arrangement of the present disclosure, and the implementation principle and the technical effect are similar, which will not be repeated herein.

Figure 26:
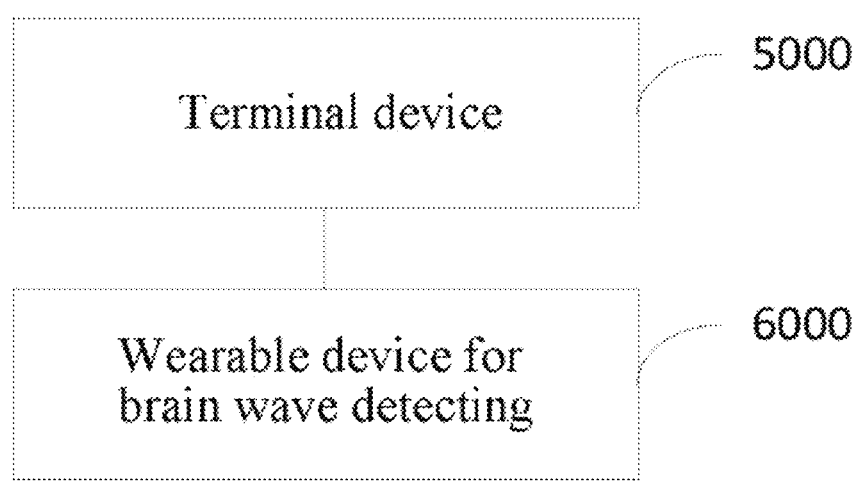
FIG. 26 is a schematic structural diagram of a photographing system based on brain wave detection according to a fifth arrangement of the present disclosure.

In order to implement the above arrangements, the present disclosure also provides a photographing system based on brain wave detection. FIG. 26 is a schematic structural diagram of a photographing system based on brain wave detection according to the fifth arrangement of the present disclosure, and as shown in FIG. 26, the system includes a terminal device 5000 having a photographing module, and a wearable device 6000 for brain wave detecting, wherein the wearable device 6000 for brain wave detecting is configured to detect a brain wave signal of the user.

The terminal device 5000 is configured to implement the photographing processing method based on brain wave detection described in the third scene.

It should be noted that, the explanation of the photographing processing method based on the brain wave detection in the third scene is also applicable to the photographing system based on the brain wave detection of the arrangement of the present disclosure, and the implementation principle and the technical effect are similar, which will not be repeated herein.

Figure 27:
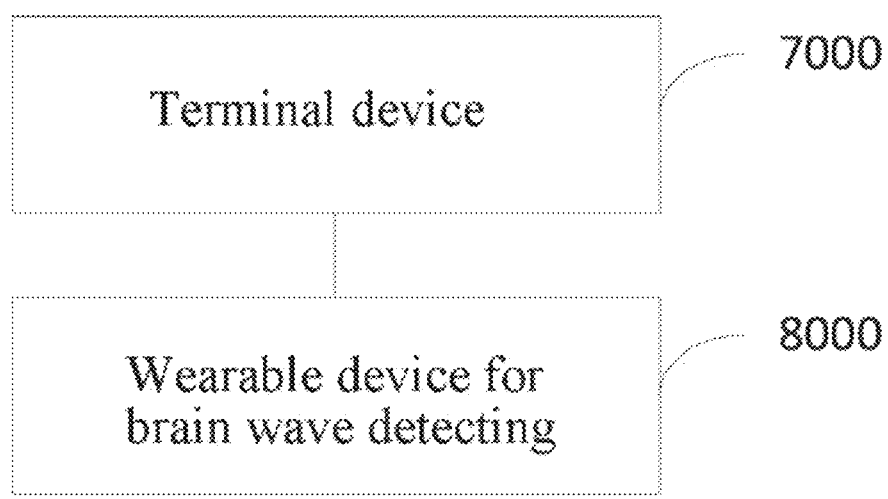
FIG. 27 is a schematic structural diagram of a photographing system based on brain wave detection according to a sixth arrangement of the present disclosure.

In order to implement the above arrangements, the present disclosure also provides a photographing system based on brain wave detection. FIG. 27 is a schematic structural diagram of a photographing system based on brain wave detection according to the sixth arrangement of the present disclosure, and as shown in FIG. 27, the system includes a terminal device 7000 having a photographing module, and a wearable device 8000 for brain wave detecting, wherein the wearable device 8000 for brain wave detecting is configured to detect a brain wave signal of the user.

The terminal device 7000 is configured to implement the photographing processing method based on brain wave detection described in the fourth scene.

It should be noted that, the explanation of the photographing processing method based on the brain wave detection in the fourth scene is also applicable to the photographing system based on the brain wave detection of the arrangement of the present disclosure, and the implementation principle and the technical effect are similar, which will not be repeated herein.

In the description of the present specification, the description with reference to the terms "one arrangement", "some arrangements", "example", "specific example", or "some examples" and the like means that a specific feature, structure, material or characteristic described in connection with the arrangement or example is included in at least one arrangement or example of the present disclosure. In the present specification, the schematic representation of the above terms is not necessarily directed to the same arrangement or example. Furthermore, the particular features, structures, materials, or characteristics described may be combined in a suitable manner in any one or more arrangements or examples. In addition, in the absence of contradiction, those skilled in the art can combine the different arrangements or examples described in the specification and the features of different arrangements or examples.

While the arrangements of the present disclosure have been shown and described above, it is understood that the above-described arrangements are illustrative and are not to be construed as limiting of the present disclosure, variations, modifications, substitutions and variations of the above-described arrangements may be made by those skilled in the art within the scope of the present disclosure.

What is claimed is:

1. A photographing processing method, applied to a terminal device including a camera, based on brain wave detection, comprising:

evaluating, by a processor of the terminal device, an emotional state of a first user based on a brain wave signal of the first user detected by a plurality of brain wave sensing metal electrodes disposed at different positions on an inner wall of a headband of the first user;

comparing, by the processor of the terminal device, a degree of the emotional state with a preset state threshold;

responsive to that the degree of the emotional state is greater than or equal to the preset state threshold, obtaining, by the processor of the terminal device, an emotional tag corresponding to the emotional state by querying a pre-stored image library; wherein the pre-stored image library is pre-stored with information of the emotional tag corresponding to the emotional state, and the emotional tag is a specific character tag, wherein the emotional state comprises happy, sad, concentration and excitement;

adding, by the processor of the terminal device, the emotional tag to a blank template preset in the camera of the terminal device;

performing, by the camera of the terminal device, image recognition on a main image;

adjusting the emotional tag to a position suitable for photographing, wherein, at the position, the emotional tag does not cover the main image;

acquiring, by the processor of the terminal device, a combined photo by combining the emotional tag into a photo taken in the emotional state, wherein the photo is taken by the camera of the terminal device;

generating an emotional log of the first user based on the combined photo;

sending, by a first mobile phone of the first user, the emotional log of the first user to a cloud server for a second user to download the emotional log from the cloud server for viewing, wherein the emotional log comprises the combined photo labeled with global positioning system (GPS) information and the emotional tag;

sending, by a second mobile phone of the second user, reminder information to the second user responsive to detecting that location information of the second user matches the GPS information labeled in the emotional log uploaded by the first user, wherein the reminder information is an information to remind the second user that the first user has been at a same location as the second user;

sending a combination scene of the combined photo corresponding to the location information and the emotional state of the first user and a current image to the second user;

converting, by a plurality of brain wave sensing metal electrodes disposed at different positions on an inner wall of a headband of the second user, the emotional tag of the first user into a corresponding brain wave to be inputted into the second user for stimulation; and inputting the corresponding brain wave into the second user for stimulation by the plurality of brain wave sensing metal electrodes, such that the second user feels emotion of the first user to achieve psychological effect of the first user.

2. The method of claim 1, wherein acquiring the combined photo by combining the emotional tag into the photo taken in the emotional state comprises:

encoding the emotional state and transmitting an encoded code stream to a driving circuit of a light emitting diode (LED) module, so that the driving circuit performs a strobe according to the encoded code stream;

generating a photo with black and white stripes according to stroboscopic information of the LED module during capturing the main image by the camera of the terminal device; and acquiring the emotional tag corresponding to information of the black and white stripes by decoding the information of the black and white stripes of the photo, and adding the emotional tag to an original photo.

3. The method of claim 1, after comparing the degree of the emotional state with the preset state threshold, the method further comprises:

stopping photographing the photo, responsive to obtaining that the degree of the emotional state is less than the state threshold.

4. The method of claim 1, wherein acquiring the combined photo by combining the emotional tag into the photo taken in the emotional state comprises:

combining the emotional tau into the combined photo taken in the emotional state in an invisible pattern, wherein the invisible pattern is one of a pattern of a two-dimensional code, an abstract picture, and a stripe image formed by flashing of visible light in high frequency;

prompting the second user to enter a viewing password responsive to the invisible pattern being triggered by the second user to send a viewing request; and upon the second user inputting the viewing password, verifying the viewing password according to a pre-stored password for a verification, and converting the invisible pattern into a visible emotional tag responsive to passing the verification.

5. The method of claim 1, further comprising:

generating an emotional audio file corresponding to the emotional state, and combining the emotional audio file into the combined photo taken in the emotional state; and playing the emotional audio file corresponding to the combined photo responsive to detecting that the combined photo is opened.

6. A wearable device for photographing based on brain wave detection, comprising:

a photographing module being a camera, a brain wave detecting module, a processor, and a memory, wherein the memory is connected to the photographing module and the brain wave detecting module, and the processor executes a program corresponding to an executable program code by reading an executable program code stored in the memory, to implement the photographing processing method based on brain wave detection according to claim 1.

7. The wearable device of claim 6, wherein the brain wave detecting module comprises:
- a plurality of brain wave sensing metal electrodes at different positions on the inner wall of the headband of a first user, wherein the plurality of brain wave sensing metal electrodes are configured to detect the brain wave signal of the first user;
- a light emitting diode (LED) module configured to perform a strobe according to an encoded code stream, wherein the encoded code stream is obtained by encoding the emotional state; and
- a wireless communication module configured to send an emotional log of the first user to a cloud server for a second user to download the emotional log from the cloud server for viewing.

* * * * *